United States Patent
Smart et al.

(10) Patent No.: US 9,958,363 B2
(45) Date of Patent: May 1, 2018

(54) FLUOROUS AFFINITY EXTRACTION FOR IONIC LIQUID-BASED SAMPLE PREPARATION

(71) Applicant: Agilent Technologies, Inc., Loveland, CA (US)

(72) Inventors: Brian Phillip Smart, San Jose, CA (US); Brooks Bond-Watts, Fremont, CA (US); James Alexander Apffel, Jr., Mountain View, CA (US)

(73) Assignee: Agilent Technologies, Inc., Santa Clara, CA (US)

( * ) Notice: Subject to any disclaimer, the term of this patent is extended or adjusted under 35 U.S.C. 154(b) by 168 days.

(21) Appl. No.: 14/724,656

(22) Filed: May 28, 2015

(65) Prior Publication Data
US 2015/0369711 A1    Dec. 24, 2015

Related U.S. Application Data

(60) Provisional application No. 62/016,000, filed on Jun. 23, 2014, provisional application No. 62/016,003, (Continued)

(51) Int. Cl.
G01N 1/00    (2006.01)
G01N 1/34    (2006.01)
(Continued)

(52) U.S. Cl.
CPC ............ *G01N 1/34* (2013.01); *B01D 11/04* (2013.01); *G01N 1/405* (2013.01); *G01N 1/4055* (2013.01);
(Continued)

(58) Field of Classification Search
CPC ...................................... G01N 1/34
(Continued)

(56) References Cited

U.S. PATENT DOCUMENTS 7,273,587 B1    9/2007 Birkner et al.
7,273,720 B1    9/2007 Birkner et al.
(Continued)

FOREIGN PATENT DOCUMENTS

WO    WO2007110637    10/2007
WO    WO2011155829    12/2011

OTHER PUBLICATIONS

Yuesheng Ye, Yossef A. Elabd "Anion exchanged polymerized ionic liquids: High free volume single ion conductors" Polymer 52 (2011) 1309-1317, plus supplementary data (pp. 1-6).*
(Continued)

*Primary Examiner* — Christine T Mui
*Assistant Examiner* — Emily R. Berkeley

(57) ABSTRACT

A method for removing an ionic liquid from an aqueous sample is provided. In some embodiments, the method includes: (a) combining an aqueous sample including an ionic liquid with an ion exchanger composition including an ion exchanger counterion to produce a solution including a fluorous salt of the ionic liquid, where at least one of the ionic liquid and the ion exchanger counterion is fluorinated; (b) contacting the solution with a fluorous affinity material, thereby removing fluorous salt from the solution and producing an aqueous eluate; and (c) collecting the aqueous eluate. In certain embodiments, the method further includes: contacting a cell with an ionic liquid composition to lyse the cell and produce an aqueous sample; and contacting the aqueous sample with a reverse phase substrate, thereby adsorbing proteins and/or lipids of the cell on the substrate. Compositions, kits and systems for practicing the subject methods are also provided.

15 Claims, 14 Drawing Sheets

Related U.S. Application Data filed on Jun. 23, 2014, provisional application No. 62/049,285, filed on Sep. 11, 2014, provisional application No. 62/051,804, filed on Sep. 17, 2014.

(51) Int. Cl.
  *B01D 11/04* (2006.01)
  *G01N 1/40* (2006.01)

(52) U.S. Cl.
  CPC .............. *Y10T 436/145555* (2015.01); *Y10T 436/147777* (2015.01); *Y10T 436/24* (2015.01)

(58) Field of Classification Search
  USPC ........................................................ 436/178
  See application file for complete search history.

(56) References Cited

U.S. PATENT DOCUMENTS

| | | | | |
|---|---|---|---|---|
| 8,143,381 | B2* | 3/2012 | Von Hagen | C07K 14/705 530/350 |
| 8,211,307 | B2 | 7/2012 | Chew et al. | |
| 2002/0072619 | A1* | 6/2002 | Bonrath | C07D 311/72 549/411 |
| 2006/0178507 | A1* | 8/2006 | Berry | C07B 63/00 536/25.3 |
| 2007/0093462 | A1* | 4/2007 | Rogers | A61K 9/143 514/184 |
| 2009/0004048 | A1 | 1/2009 | Elliott et al. | |
| 2011/0124034 | A1 | 5/2011 | Kuehnle et al. | |
| 2011/0192793 | A1* | 8/2011 | Chew | C12N 1/06 210/633 |
| 2014/0273080 | A1 | 9/2014 | Apffel, Jr. | |

OTHER PUBLICATIONS

Wei Ren, Aaron M. Scurto "Phase equilibria of imidazolium ionic liquids and the refrigerant gas, 1,1,1,2-tetrafluoroethane (R-134a)" Fluid Phase Equilibria 286 (2009) 1-7.*

Mark B. Shiflett and A. Yokozeki "Liquid-Liquid Equilibria of Hydrofluoroethers and Ionic Liquid 1-Ethyl-3-methylimidazolium Bis(trifluoromethylsulfonyl)imide" J. Chem. Eng. Data 2007, 52, 2413-2418.*

Lu, et al., "A Bioelectrochemical Method for the Quantitative Description of the Hofmeister Effect of Ionic Liquids in Aqueous Solution", J. Phys. Chem., 2012, 116, 11075-11080.

Rezaee, et al., "Determination of organic compounds in water using dispersive liquid-liquid microextraction", Journal of Chromatography A, 1116, 2006,1-9.

Shahriari, et al., "Role of the Hofmeister Series in the Formation of Ionic-Liquid-Based Aqueous Biphase Systems", J. Phys. Chem., 2012, 116, 7252-7258.

Yao, et al., "Dispersive liquid-liquid microextraction using an in situ metathesis reaction to form an ionic liquid extraction phase for the preconcentration of aromatic compounds from water", Anal Bioanal Chem., 2009, 395:1491-1502.

* cited by examiner

Yeast cells
100uL water

Yeast cells
50uL water 50 uL HMIM-Cl

FLUOROUS AFFINITY EXTRACTION FOR IONIC LIQUID-BASED SAMPLE PREPARATION

CROSS-REFERENCING

This patent application claims the benefit of U.S. provisional application Ser. Nos. 62/016,003, filed on Jun. 23, 2014, 62/051,804, filed on Sep. 17, 2014, 62/049,285, filed on Sep. 11, 2014 and 62/016,000, filed on Jun. 23, 2014, which applications are incorporated herein by reference for all purposes.

INTRODUCTION

Sample preparation is an analytical process which includes an extraction procedure that results in the isolation and enrichment of components of interest from a sample matrix. Extraction can vary in degree of selectivity, speed and convenience and depends not only on the approach and conditions used but also on the geometric configurations of the extraction phase. There is a constant need for the development of simplified and miniaturized sample preparation methods requiring lower quantities of purification materials and more efficient ways to obtain isolated and purified analytical samples.

SUMMARY

Aspects of the present disclosure include a method for removing an ionic liquid from an aqueous sample. In some embodiments, the method includes: (a) combining an aqueous sample including an ionic liquid with an ion exchanger composition including an ion exchanger counterion to produce a solution including a fluorous salt of the ionic liquid, wherein at least one of the ionic liquid and the ion exchanger counterion is fluorinated; (b) contacting the solution with a fluorous affinity material, thereby removing fluorous salt from the solution and producing an aqueous eluate; and (c) collecting the aqueous eluate. In some cases, the fluorous affinity material is an immiscible fluorous solvent that extracts the fluorous salt from the solution to produce the aqueous eluate. In certain embodiments, prior to step (a), the method includes: contacting a cell with an amount of an ionic liquid composition sufficient to lyse the cell and produce an aqueous sample including an ionic liquid; and contacting the aqueous sample with a reverse phase substrate, thereby adsorbing proteins and/or lipids of the cell on the reverse phase substrate and producing a contacted aqueous sample. Also provided are compositions including: a fluorous salt of an ionic liquid; and a fluorous solvent. Kits and systems for practicing the subject methods are also provided.

BRIEF DESCRIPTION OF THE FIGURES

The skilled artisan will understand that the drawings, described below, are for illustration purposes only. The drawings are not intended to limit the scope of the present teachings in any way.

DEFINITIONS

Figure 1:
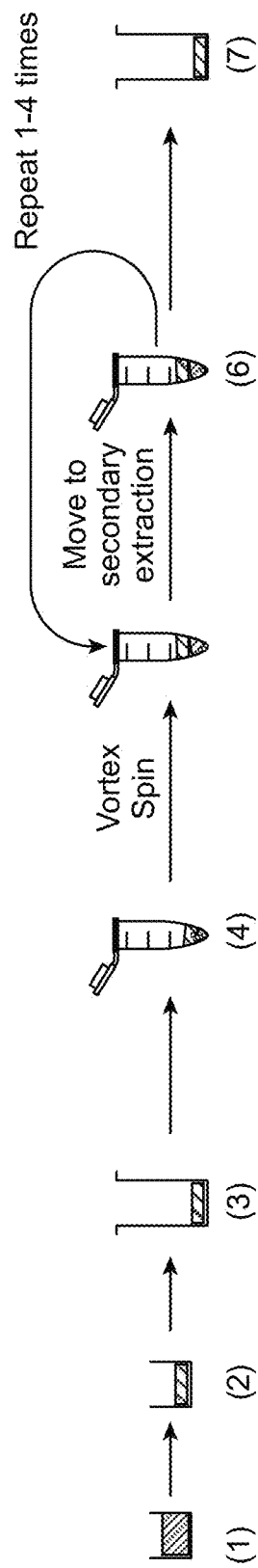
FIG. 1 schematically illustrates an ionic liquid metabolomics sample preparation workflow for methods according one embodiment of the subject method: (1) Fast filter; (2) Lyse/Quench 50 µL 1:1 IL:$H_2O$; (3) C18 column (remove protein and lipids); (4) Extract IL 225 µL $H_2O$, 100 µL fluorous solvent, 1.1 equivalents $M^{+-}NTf_n$; (6) 50 µL $H_2O$, 50 µL fluorous solvent, 0.05 equivalents $M^{+-}NTf_n$; (7) fluorous SPE (maybe not needed).

Before describing exemplary embodiments in greater detail, the following definitions are set forth to illustrate and define the meaning and scope of the terms used in the description.

Unless defined otherwise, all technical and scientific terms used herein have the same meaning as commonly understood by one of ordinary skill in the art to which this invention belongs. Singleton, et al., DICTIONARY OF MICROBIOLOGY AND MOLECULAR BIOLOGY, 2D ED., John Wiley and Sons, New York (1994), and Hale & Markham, THE HARPER COLLINS DICTIONARY OF BIOLOGY, Harper Perennial, N.Y. (1991) provide one of skill with the general meaning of many of the terms used herein. Still, certain terms are defined below for the sake of clarity and ease of reference.

It must be noted that as used herein and in the appended claims, the singular forms "a", "an", and "the" include plural referents unless the context clearly dictates otherwise. For example, the term "a primer" refers to one or more primers, i.e., a single primer and multiple primers. It is further noted that the claims can be drafted to exclude any optional element. As such, this statement is intended to serve as antecedent basis for use of such exclusive terminology as "solely," "only" and the like in connection with the recitation of claim elements, or use of a "negative" limitation.

The term "sample" as used herein relates to a material or mixture of materials, typically, although not necessarily, in liquid form, containing one or more analytes of interest. In one embodiment, the term as used in its broadest sense, refers to any plant, animal or bacterial material containing cells or producing cellular metabolites, such as, for example, tissue or fluid isolated from an individual (including without limitation plasma, serum, cerebrospinal fluid, lymph, tears, saliva and tissue sections) or from in vitro cell culture constituents, as well as samples from the environment. The term "sample" may also refer to a "biological sample". As used herein, the term "a biological sample" refers to a whole organism or a subset of its tissues, cells or component parts (e.g. body fluids, including but not limited to blood, mucus, lymphatic fluid, synovial fluid, cerebrospinal fluid, saliva, amniotic fluid, amniotic cord blood, urine, vaginal fluid and semen). A "biological sample" can also refer to a homogenate, lysate or extract prepared from a whole organism or a subset of its tissues, cells or component parts, or a fraction or portion thereof, including but not limited to, for example, plasma, serum, spinal fluid, lymph fluid, the external sections of the skin, respiratory, intestinal, and genitourinary tracts, tears, saliva, milk, blood cells, tumors, organs. In certain embodiments, the sample has been removed from an animal or plant. Biological samples of the invention include cells. The term "cells" is used in its conventional sense to refer to the basic structural unit of living organisms, both eukaryotic and prokaryotic, having at least a nucleus and a cell membrane. In certain embodiments, cells include prokaryotic cells, such as from bacteria. In other embodiments, cells include eukaryotic cells, such as cells obtained from biological samples from animals, plants or fungi.

The term "denaturing," as used herein, refers to the process in which proteins or nucleic acids lose tertiary and secondary structure which is present in the native state by the application of some external stress or compound, such as an acid or base, a concentrated inorganic salt, an organic solvent or heat. Protein denaturation includes enzyme denaturation where quaternary denaturation includes protein subunits being dissociated or the spatial arrangement of protein subunits being disrupted. Protein denaturation may further include tertiary structure denaturation which includes the disruption of covalent interactions between amino acid side chains (such as disulfide bridges between cysteine groups), non-covalent dipole-dipole interactions between polar amino acid side chains and surrounding media, Van der Waals interactions (e.g., induced dipole moments) between non-polar amino acid side chains. Protein denaturation may further include secondary structure denaturation where proteins, including enzymes lose all regular repeating patterns such as alpha-helices and beta-pleated sheets and may adopt a random-coil type configuration. Protein denaturation does not disrupt or change covalent peptide bonds or the sequence of amino acids held together (i.e., does not disrupt primary structure).

The terms "determining", "measuring", "evaluating", "assessing," "assaying," and "analyzing" are used interchangeably herein to refer to any form of measurement, and include determining if an element is present or not. These terms include both quantitative and/or qualitative determinations. Assessing may be relative or absolute. "Assessing the presence of" includes determining the amount of something present, as well as determining whether it is present or absent.

Furthermore, except as otherwise noted, the chemical methods and techniques of the present embodiments are generally performed according to conventional methods well known in the art and as described in various general and more specific references that are cited and discussed throughout the present specification. See, e.g., Loudon, Organic Chemistry, Fourth Edition, New York: Oxford University Press, 2002, pp. 360-361, 1084-1085; Smith and March, March's Advanced Organic Chemistry: Reactions, Mechanisms, and Structure, Fifth Edition, Wiley-Interscience, 2001.

Many general references providing commonly known chemical synthetic schemes and conditions useful for synthesizing the disclosed compounds are available (see, e.g., Smith and March, March's Advanced Organic Chemistry: Reactions, Mechanisms, and Structure, Fifth Edition, Wiley-Interscience, 2001; or Vogel, A Textbook of Practical Organic Chemistry, Including Qualitative Organic Analysis, Fourth Edition, New York: Longman, 1978).

Where compounds described herein contain one or more chiral centers and/or double-bond isomers (i.e., geometric isomers), enantiomers or diastereomers, all possible enantiomers and stereoisomers of the compounds including the stereoisomerically pure form (e.g., geometrically pure, enantiomerically pure or diastereomerically pure) and enantiomeric and stereoisomeric mixtures are included in the description of the compounds herein. Enantiomeric and stereoisomeric mixtures can be resolved into their component enantiomers or stereoisomers using separation techniques or chiral synthesis techniques well known to the skilled artisan. The compounds can also exist in several tautomeric forms including the enol form, the keto form and mixtures thereof. Accordingly, the chemical structures depicted herein encompass all possible tautomeric forms of the illustrated compounds. The compounds described also include isotopically labeled compounds where one or more atoms have an atomic mass different from the atomic mass conventionally found in nature. Examples of isotopes that can be incorporated into the compounds disclosed herein include, but are not limited to, $^2$H, $^3$H, $^{11}$C, $^{14}$C, $^{15}$N, $^{18}$O, $^{17}$O, etc. Compounds can exist in unsolvated forms as well as solvated forms, including hydrated forms. In general, compounds can be hydrated or solvated. Certain compounds can exist in multiple crystalline or amorphous forms. In general, all physical forms are equivalent for the uses contemplated herein and are intended to be within the scope of the present disclosure.

As used herein, the term "alkyl" by itself or as part of another substituent refers to a saturated branched or straight-chain monovalent hydrocarbon radical derived by the removal of one hydrogen atom from a single carbon atom of a parent alkane. Typical alkyl groups include, but are not limited to, methyl; ethyl, propyls such as propan-1-yl or propan-2-yl; and butyls such as butan-1-yl, butan-2-yl, 2-methyl-propan-1-yl or 2-methyl-propan-2-yl. In some embodiments, an alkyl group includes from 1 to 20 carbon atoms. In other embodiments, an alkyl group includes from 1 to 10 carbon atoms. In still other embodiments, an alkyl group includes from 1 to 6 carbon atoms, such as from 1 to 4 carbon atoms.

"Alkanyl" by itself or as part of another substituent refers to a saturated branched, straight-chain or cyclic alkyl radical derived by the removal of one hydrogen atom from a single carbon atom of an alkane. Typical alkanyl groups include, but are not limited to, methanyl; ethanyl; propanyls such as propan-1-yl, propan-2-yl (isopropyl), cyclopropan-1-yl, etc.; butanyls such as butan-1-yl, butan-2-yl (sec-butyl), 2-methyl-propan-1-yl (isobutyl), 2-methyl-propan-2-yl (t-butyl), cyclobutan-1-yl, etc.; and the like.

"Alkylene" refers to a branched or unbranched saturated hydrocarbon chain, usually having from 1 to 40 carbon atoms, more usually 1 to 10 carbon atoms and even more usually 1 to 6 carbon atoms. This term is exemplified by groups such as methylene (—CH$_2$—), ethylene (—CH$_2$CH$_2$—), the propylene isomers (e.g., —CH$_2$CH$_2$CH$_2$— and —CH(CH$_3$)CH$_2$—) and the like.

"Alkenyl" by itself or as part of another substituent refers to an unsaturated branched, straight-chain or cyclic alkyl radical having at least one carbon-carbon double bond derived by the removal of one hydrogen atom from a single carbon atom of an alkene. The group may be in either the cis or trans conformation about the double bond(s). Typical alkenyl groups include, but are not limited to, ethenyl; propenyls such as prop-1-en-1-yl, prop-1-en-2-yl, prop-2-en-1-yl (allyl), prop-2-en-2-yl, cycloprop-1-en-1-yl; cycloprop-2-en-1-yl; butenyls such as but-1-en-1-yl, but-1-en-2-yl, 2-methyl-prop-1-en-1-yl, but-2-en-1-yl, but-2-en-1-yl, but-2-en-2-yl, buta-1,3-dien-1-yl, buta-1,3-dien-2-yl, cyclobut-1-en-1-yl, cyclobut-1-en-3-yl, cyclobuta-1,3-dien-1-yl, etc.; and the like.

"Alkynyl" by itself or as part of another substituent refers to an unsaturated branched, straight-chain or cyclic alkyl radical having at least one carbon-carbon triple bond derived by the removal of one hydrogen atom from a single carbon atom of an alkyne. Typical alkynyl groups include, but are not limited to, ethynyl; propynyls such as prop-1-yn-1-yl, prop-2-yn-1-yl, etc.; butynyls such as but-1-yn-1-yl, but-1-yn-3-yl, but-3-yn-1-yl, etc.; and the like.

"Acyl" by itself or as part of another substituent refers to a radical —C(O)R$^{30}$, where R$^{30}$ is hydrogen, alkyl, cycloalkyl, cycloheteroalkyl, aryl, arylalkyl, heteroalkyl, heteroaryl, heteroarylalkyl as defined herein and substituted versions thereof. Representative examples include, but are not limited to formyl, acetyl, cyclohexylcarbonyl, cyclohexylmethylcarbonyl, benzoyl, benzylcarbonyl, piperonyl, succinyl, and malonyl, and the like.

The term "aminoacyl" refers to the group —C(O)NR$^{21}$R$^{22}$, wherein R$^{21}$ and R$^{22}$ independently are selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, and substituted heterocyclic and where R$^{21}$ and R$^{22}$ are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Alkoxy" by itself or as part of another substituent refers to a radical —OR$^{31}$ where R$^{31}$ represents an alkyl or cycloalkyl group as defined herein. Representative examples include, but are not limited to, methoxy, ethoxy, propoxy, butoxy, cyclohexyloxy and the like.

"Alkoxycarbonyl" by itself or as part of another substituent refers to a radical —C(O)OR$^{31}$ where R$^{31}$ represents an alkyl or cycloalkyl group as defined herein. Representative examples include, but are not limited to, methoxycarbonyl, ethoxycarbonyl, propoxycarbonyl, butoxycarbonyl, cyclohexyloxycarbonyl and the like.

"Aryl" by itself or as part of another substituent refers to a monovalent aromatic hydrocarbon radical derived by the removal of one hydrogen atom from a single carbon atom of an aromatic ring system. Typical aryl groups include, but are not limited to, groups derived from aceanthrylene, acenaphthylene, acephenanthrylene, anthracene, azulene, benzene, chrysene, coronene, fluoranthene, fluorene, hexacene, hexaphene, hexalene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene, trinaphthalene and the like. In certain embodiments, an aryl group includes from 6 to 20 carbon atoms. In certain embodiments, an aryl group includes from 6 to 12 carbon atoms. Examples of an aryl group are phenyl and naphthyl.

"Arylalkyl" by itself or as part of another substituent refers to an acyclic alkyl radical in which one of the hydrogen atoms bonded to a carbon atom, typically a terminal or sp$^3$ carbon atom, is replaced with an aryl group. Typical arylalkyl groups include, but are not limited to, benzyl, 2-phenylethan-1-yl, 2-phenylethen-1-yl, naphthylmethyl, 2-naphthylethan-1-yl, 2-naphthylethen-1-yl, naphthobenzyl, 2-naphthophenylethan-1-yl and the like. Where specific alkyl moieties are intended, the nomenclature arylalkanyl, arylalkenyl and/or arylalkynyl is used. In certain embodiments, an arylalkyl group is (C$_7$-C$_{30}$) arylalkyl, e.g., the alkanyl, alkenyl or alkynyl moiety of the arylalkyl group is (C$_1$-C$_{10}$) and the aryl moiety is (C$_6$-C$_{20}$). In certain embodiments, an arylalkyl group is (C$_7$-C$_{20}$) arylalkyl, e.g., the alkanyl, alkenyl or alkynyl moiety of the arylalkyl group is (C$_1$-C$_8$) and the aryl moiety is (C$_6$-C$_{12}$).

"Arylaryl" by itself or as part of another substituent, refers to a monovalent hydrocarbon group derived by the removal of one hydrogen atom from a single carbon atom of a ring system in which two or more identical or non-identical aromatic ring systems are joined directly together by a single bond, where the number of such direct ring junctions is one less than the number of aromatic ring systems involved. Typical arylaryl groups include, but are not limited to, biphenyl, triphenyl, phenyl-napthyl, binaphthyl, biphenyl-napthyl, and the like. When the number of carbon atoms in an arylaryl group are specified, the numbers refer to the carbon atoms including each aromatic ring. For example, ($C_5$-$C_{14}$) arylaryl is an arylaryl group in which each aromatic ring includes from 5 to 14 carbons, e.g., biphenyl, triphenyl, binaphthyl, phenylnapthyl, etc. In certain embodiments, each aromatic ring system of an arylaryl group is independently a ($C_5$-$C_{14}$) aromatic. In certain embodiments, each aromatic ring system of an arylaryl group is independently a ($C_5$-$C_{10}$) aromatic. In certain embodiments, each aromatic ring system is identical, e.g., biphenyl, triphenyl, binaphthyl, trinaphthyl, etc.

"Cycloalkyl" by itself or as part of another substituent refers to a saturated or unsaturated cyclic alkyl radical. Where a specific level of saturation is intended, the nomenclature "cycloalkanyl" or "cycloalkenyl" is used. Typical cycloalkyl groups include, but are not limited to, groups derived from cyclopropane, cyclobutane, cyclopentane, cyclohexane and the like. In certain embodiments, the cycloalkyl group is ($C_3$-$C_{10}$) cycloalkyl. In certain embodiments, the cycloalkyl group is ($C_3$-$C_7$) cycloalkyl.

"Cycloheteroalkyl" or "heterocyclyl" by itself or as part of another substituent, refers to a saturated or unsaturated cyclic alkyl radical in which one or more carbon atoms (and any associated hydrogen atoms) are independently replaced with the same or different heteroatom. Typical heteroatoms to replace the carbon atom(s) include, but are not limited to, N, P, O, S, Si, etc. Where a specific level of saturation is intended, the nomenclature "cycloheteroalkanyl" or "cycloheteroalkenyl" is used. Typical cycloheteroalkyl groups include, but are not limited to, groups derived from epoxides, azirines, thiiranes, imidazolidine, morpholine, piperazine, piperidine, pyrazolidine, pyrrolidine, quinuclidine and the like.

"Heteroalkyl, Heteroalkanyl, Heteroalkenyl and Heteroalkynyl" by themselves or as part of another substituent refer to alkyl, alkanyl, alkenyl and alkynyl groups, respectively, in which one or more of the carbon atoms (and any associated hydrogen atoms) are independently replaced with the same or different heteroatomic groups. Typical heteroatomic groups which can be included in these groups include, but are not limited to, —O—, —S—, —S—S—, —O—S—, —N$R^{37}R^{38}$—, =N—N=, —N=N—, —N=N—N$R^{39}R^{40}$, —P$R^{41}$—, P(O)$_2$—, —PO$R^{42}$—, —O—P(O)$_2$—, —S—O—, —S—(O)—, —SO$_2$—, —Sn$R^{43}R^{44}$— and the like, where $R^{37}$, $R^{38}$, $R^{39}$, $R^{40}$, $R^{41}$, $R^{42}$, $R^{43}$, and $R^{44}$ are independently hydrogen, alkyl, substituted alkyl, aryl, substituted aryl, arylalkyl, substituted arylalkyl, cycloalkyl, substituted cycloalkyl, cycloheteroalkyl, substituted cycloheteroalkyl, heteroalkyl, substituted heteroalkyl, heteroaryl, substituted heteroaryl, heteroarylalkyl or substituted heteroarylalkyl.

"Heteroaryl" by itself or as part of another substituent, refers to a monovalent heteroaromatic radical derived by the removal of one hydrogen atom from a single atom of a heteroaromatic ring system. Typical heteroaryl groups include, but are not limited to, groups derived from acridine, arsindole, carbazole, β-carboline, chromane, chromene, cinnoline, furan, imidazole, indazole, indole, indoline, indolizine, isobenzofuran, isochromene, isoindole, isoindoline, isoquinoline, isothiazole, isoxazole, naphthyridine, oxadiazole, oxazole, perimidine, phenanthridine, phenanthroline, phenazine, phthalazine, pteridine, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, xanthene, benzodioxole and the like. In certain embodiments, the heteroaryl group is from 5-20 membered heteroaryl. In certain embodiments, the heteroaryl group is from 5-10 membered heteroaryl. In certain embodiments, heteroaryl groups are those derived from thiophene, pyrrole, benzothiophene, benzofuran, indole, pyridine, quinoline, imidazole, oxazole and pyrazine.

"Heteroarylalkyl" by itself or as part of another substituent, refers to an acyclic alkyl radical in which one of the hydrogen atoms bonded to a carbon atom, typically a terminal or $sp^a$ carbon atom, is replaced with a heteroaryl group. Where specific alkyl moieties are intended, the nomenclature heteroarylalkanyl, heteroarylalkenyl and/or heterorylalkynyl is used. In certain embodiments, the heteroarylalkyl group is a 6-30 membered heteroarylalkyl, e.g., the alkanyl, alkenyl or alkynyl moiety of the heteroarylalkyl is 1-10 membered and the heteroaryl moiety is a 5-20-membered heteroaryl. In certain embodiments, the heteroarylalkyl group is 6-20 membered heteroarylalkyl, e.g., the alkanyl, alkenyl or alkynyl moiety of the heteroarylalkyl is 1-8 membered and the heteroaryl moiety is a 5-12-membered heteroaryl.

"Aromatic Ring System" by itself or as part of another substituent, refers to an unsaturated cyclic or polycyclic ring system having a conjugated π electron system. Specifically included within the definition of "aromatic ring system" are fused ring systems in which one or more of the rings are aromatic and one or more of the rings are saturated or unsaturated, such as, for example, fluorene, indane, indene, phenalene, etc. Typical aromatic ring systems include, but are not limited to, aceanthrylene, acenaphthylene, acephenanthrylene, anthracene, azulene, benzene, chrysene, coronene, fluoranthene, fluorene, hexacene, hexaphene, hexalene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene, trinaphthalene and the like.

"Heteroaromatic Ring System" by itself or as part of another substituent, refers to an aromatic ring system in which one or more carbon atoms (and any associated hydrogen atoms) are independently replaced with the same or different heteroatom. Typical heteroatoms to replace the carbon atoms include, but are not limited to, N, P, O, S, Si, etc. Specifically included within the definition of "heteroaromatic ring systems" are fused ring systems in which one or more of the rings are aromatic and one or more of the rings are saturated or unsaturated, such as, for example, arsindole, benzodioxan, benzofuran, chromane, chromene, indole, indoline, xanthene, etc. Typical heteroaromatic ring systems include, but are not limited to, arsindole, carbazole, β-carboline, chromane, chromene, cinnoline, furan, imidazole, indazole, indole, indoline, indolizine, isobenzofuran, isochromene, isoindole, isoindoline, isoquinoline, isothiazole, isoxazole, naphthyridine, oxadiazole, oxazole, perimidine, phenanthridine, phenanthroline, phenazine, phthalazine, pteridine, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, xanthene and the like.

"Substituted" refers to a group in which one or more hydrogen atoms are independently replaced with the same or different substituent(s). Typical substituents include, but are not limited to, alkylenedioxy (such as methylenedioxy), -M, —$R^{60}$, —$O^-$, =$O$, —$OR^{60}$, —$SR^{60}$, —$S^-$, =$S$, —$NR^{60}R^{61}$, =$NR^{60}$, —$CF_3$, —$CN$, —$OCN$, —$SCN$, —$NO$, —$NO_2$, =$N_2$, —$N_3$, —$S(O)_2O^-$, —$S(O)_2OH$, —$S(O)_2R^{60}$, —$OS(O)_2O^-$, —$OS(O)_2R^{60}$, —$P(O)(O^-)_2$, —$P(O)(OR^{60})(O^-)$, —$OP(O)(OR^{60})(OR^{61})$, —$C(O)R^{60}$, —$C(S)R^{60}$, —$C(O)OR^{60}$, —$C(O)NR^{60}R^{61}$, —$C(O)O^-$, —$C(S)OR^{60}$, —$NR^{62}C(O)NR^{60}R^{61}$, —$NR^{62}C(S)NR^{60}R^{61}$, —$NR^{62}C(NR^{63})NR^{60}R^{61}$ and —$C(NR^{62})NR^{60}R^{61}$ where M is halogen; $R^{60}$, $R^{61}$, $R^{62}$ and $R^{63}$ are independently hydrogen, alkyl, substituted alkyl, alkoxy, substituted alkoxy, cycloalkyl, substituted cycloalkyl, cycloheteroalkyl, substituted cycloheteroalkyl, aryl, substituted aryl, heteroaryl or substituted heteroaryl, or optionally $R^{60}$ and $R^{61}$ together with the nitrogen atom to which they are bonded form a cycloheteroalkyl or substituted cycloheteroalkyl ring; and $R^{64}$ and $R^{65}$ are independently hydrogen, alkyl, substituted alkyl, aryl, cycloalkyl, substituted cycloalkyl, cycloheteroalkyl, substituted cycloheteroalkyl, aryl, substituted aryl, heteroaryl or substituted heteroaryl, or optionally $R^{64}$ and $R^{65}$ together with the nitrogen atom to which they are bonded form a cycloheteroalkyl or substituted cycloheteroalkyl ring. In certain embodiments, substituents include -M, —$R^{60}$, =$O$, —$OR^{60}$, —$SR^{60}$, —$S^-$, =$S$, —$NR^{60}R^{61}$, =$NR^{60}$, —$CF_3$, —$CN$, —$OCN$, —$SCN$, —$NO$, —$NO_2$, =$N_2$, —$N_3$, —$S(O)_2R^{60}$, —$OS(O)_2O^-$, —$OS(O)_2R^{60}$, $P(O)(O^-)_2$, —$P(O)(OR^{60})(O^-)$, —$OP(O)(OR^{60})(OR^{61})$, —$C(O)R^{60}$, —$C(S)R^{60}$, —$C(O)OR^{60}$, —$C(O)NR^{60}R^{61}$, —$C(O)O^-$, —$NR^{62}C(O)NR^{60}R^{61}$. In certain embodiments, substituents include -M, —$R^{60}$, =$O$, —$OR^{60}$, —$SR^{60}$, —$NR^{60}R^{61}$, —$CF_3$, —$CN$, —$NO_2$, —$S(O)_2R^{60}$, —$OP(O)(OR^{60})(OR^{61})$, —$C(O)R^{60}$, —$C(O)OR^{60}$, —$C(O)NR^{60}R^{61}$, —$C(O)O^-$. In certain embodiments, substituents include -M, —$R^{60}$, =$O$, —$OR^{60}$, —$SR^{60}$, —$NR^{60}R^{61}$, —$CF_3$, —$CN$, —$NO_2$, —$S(O)_2R^{60}$, —$C(O)R^{60}$, —$C(O)$ $OR^{60}$, —$C(O)O^-$, where $R^{60}$, $R^{61}$ and $R^{62}$ are as defined above. For example, a substituted group may bear a methylenedioxy substituent or one, two, or three substituents selected from a halogen atom, a (1-4C)alkyl group and a (1-4C)alkoxy group.

A "plurality" contains at least 2 members. In certain cases, a plurality may have at least 10, at least 100, at least 100, at least 10,000, at least 100,000, at least $10^6$, at least $10^7$, at least $10^8$ or at least $10^9$ or more members.

Numeric ranges are inclusive of the numbers defining the range.

The term "separating", as used herein, refers to physical separation of two elements (e.g., by size or affinity, etc.) as well as degradation of one element, leaving the other intact.

The term "sample" as used herein relates to a material or mixture of materials, typically, although not necessarily, in fluid, i.e., aqueous, form, containing one or more components of interest. Samples may be derived from a variety of sources such as from food stuffs, environmental materials, a biological sample or solid, such as tissue or fluid isolated from an individual, including but not limited to, for example, plasma, serum, spinal fluid, semen, lymph fluid, the external sections of the skin, respiratory, intestinal, and genitourinary tracts, tears, saliva, milk, blood cells, tumors, organs, and also samples of in vitro cell culture constituents (including but not limited to conditioned medium resulting from the growth of cells in cell culture medium, putatively virally infected cells, recombinant cells, and cell components).

Components in a sample may be termed "analytes". In many embodiments, the sample is a complex sample containing at least about $10^2$, $5 \times 10^2$, $10^3$, $5 \times 10^3$, $10^4$, $5 \times 10^4$, $10^5$, $5 \times 10^5$, $10^6$, $5 \times 10^6$, $10^7$, $5 \times 10^7$, $10^8$, $10^9$, $10^{10}$, $10^{11}$, $10^{12}$ or more species of analyte.

The term "analyte" are used herein interchangeably and refer to a known or unknown component of a sample, which will specifically bind to a capture agent on a substrate surface if the analyte and the molecular probe are members of a specific binding pair. In general, analytes are biopolymers, i.e., an oligomer or polymer such as an oligonucleotide, a peptide, a polypeptide, an antibody, or the like. In this case, an "analyte" is referenced as a moiety in a mobile phase (typically fluid), to be detected by a "capture agent" which, in most embodiments, is bound to a substrate. However, either of the "analyte" or "capture agent" may be the one which is to be evaluated by the other (thus, either one could be an unknown mixture of analytes, e.g., polypeptides, to be evaluated by binding with the other).

The term "biological sample" is used herein to refer to a whole organism, plant, fungi or a subset of animal tissues, cells or component parts which may in certain instances be found in blood, mucus, lymphatic fluid, synovial fluid, cerebrospinal fluid, saliva, amniotic fluid, amniotic cord blood, urine, vaginal fluid and semen. As such, a "biological sample" used herein can refer to a homogenate, lysate or extract prepared from a whole organism or a subset of its tissues, including but not limited to, for example, plasma, serum, spinal fluid, lymph fluid, the external sections of the skin, respiratory, intestinal, and genitourinary tracts, tears, saliva, milk, blood cells, tumors, organs. In embodiments of the invention, a "biological sample" will contain cells from the animal, plants, bacteria or fungi. A "biological sample" can also refer to a medium, such as a nutrient broth or gel in which an organism has been propagated, which contains cells as well as cellular components, such as proteins or nucleic acid molecules. Biological samples of the invention include cells. The term "cells" is used in its conventional sense to refer to the basic structural unit of living organisms, both eukaryotic and prokaryotic, having at least a nucleus and a cell membrane. In certain embodiments, cells include prokaryotic cells, such as from bacteria. In other embodiments, cells include eukaryotic cells, such as cells obtained from biological samples from animals, plants or fungi.

The methods described herein include multiple steps. Each step may be performed after a predetermined amount of time has elapsed between steps, as desired. As such, the time between performing each step may be 1 second or more, 10 seconds or more, 30 seconds or more, 60 seconds or more, 5 minutes or more, 10 minutes or more, 60 minutes or more and including 5 hours or more. In certain embodiments, each subsequent step is performed immediately after completion of the previous step. In other embodiments, a step may be performed after an incubation or waiting time after completion of the previous step, e.g., a few minutes to an overnight waiting time.

Other definitions of terms may appear throughout the specification.

DESCRIPTION OF EXEMPLARY EMBODIMENTS

As summarized above, aspects of the present disclosure include a method for removing an ionic liquid from an aqueous sample. In some embodiments, the method includes: (a) combining an aqueous sample including an ionic liquid with an ion exchanger composition including an ion exchanger counterion to produce a solution including a fluorous salt of the ionic liquid, wherein at least one of the ionic liquid and the ion exchanger counterion is fluorinated; (b) contacting the solution with a fluorous affinity material, thereby removing fluorous salt from the solution and producing an aqueous eluate; and (c) collecting the aqueous eluate. In some cases, the fluorous affinity material is an immiscible fluorous solvent that extracts the fluorous salt from the solution to produce the aqueous eluate. In certain embodiments, prior to step (a), the method includes: contacting a cell with an amount of an ionic liquid composition sufficient to lyse the cell and produce an aqueous sample including an ionic liquid; and contacting the aqueous sample with a reverse phase substrate, thereby adsorbing proteins and/or lipids of the cell on the reverse phase substrate and producing a contacted aqueous sample. Also provided are compositions including: a fluorous salt of an ionic liquid; and a fluorous solvent. Kits and systems for practicing the subject methods are also provided.

Before the various embodiments are described, it is to be understood that the teachings of this disclosure are not limited to the particular embodiments described, and as such can, of course, vary. It is also to be understood that the terminology used herein is for the purpose of describing particular embodiments only, and is not intended to be limiting, since the scope of the present teachings will be limited only by the appended claims.

The section headings used herein are for organizational purposes only and are not to be construed as limiting the subject matter described in any way. While the present teachings are described in conjunction with various embodiments, it is not intended that the present teachings be limited to such embodiments. On the contrary, the present teachings encompass various alternatives, modifications, and equivalents, as will be appreciated by those of skill in the art.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present teachings, some exemplary methods and materials are now described.

The citation of any publication is for its disclosure prior to the filing date and should not be construed as an admission that the present claims are not entitled to antedate such publication by virtue of prior invention. Further, the dates of publication provided can be different from the actual publication dates which can be independently confirmed.

As will be apparent to those of skill in the art upon reading this disclosure, each of the individual embodiments described and illustrated herein has discrete components and features which can be readily separated from or combined with the features of any of the other several embodiments without departing from the scope or spirit of the present teachings. Any recited method can be carried out in the order of events recited or in any other order which is logically possible.

All patents and publications, including all sequences disclosed within such patents and publications, referred to herein are expressly incorporated by reference.

In further describing the subject invention, methods and compositions for removing an ionic liquid from an aqueous sample, are described. Next, methods and compositions for extracting and purifying compounds from a biological sample having cells using an ionic liquid are reviewed. Compositions, kits and systems are also described.

Methods for Removing an Ionic Liquid from an Aqueous Sample

Aspects of the present disclosure include a method for removing an ionic liquid from an aqueous sample. Ionic liquids are a class of diverse organic salts having relatively low melting points which find use in a variety of applications, e.g., as organic solvent substitutes, or cell membrane disrupters.

Any convenient aqueous samples that include an ionic salt may find use in the subject methods. Samples of interest include, but are not limited to, food samples, environmental samples and biological samples. In some embodiments, the aqueous sample includes an analyte of interest, such as a metabolite of interest (e.g., as described herein). The subject methods find use in removing an ionic liquid from an aqueous sample to provide a sample suitable for analysis of a target analyte. In some cases, the ionic liquid has a detrimental effect on the analysis of the aqueous sample and removal of the ionic liquid provides for the elimination of this detrimental effect. In some cases, the aqueous sample is derived from a biological sample that includes an ionic liquid such as a cellular sample (e.g., as described herein). In certain instances, the target analyte is a metabolite. In certain instances, the target analyte is a protein. In certain instances, the target analyte is a lipid.

The subject methods and compositions find use in the removal of an ionic liquid from an aqueous sample of interest using any one of a variety of methods including, but not limited to, extraction, chromatography, immobilization and separation (e.g., using a magnetic field). In general terms, the method includes producing a salt of the ionic liquid and an ion exchanger counterion, which salt may have a physical or chemical property that provides for preferential removal of the salt from the aqueous sample using a suitable method (e.g., as described herein). In some instances, an ionic liquid may be removed via the immobilization of a magnetic composition, e.g., via the application of a magnetic field to isolate a magnetic salt of the ionic liquid and the ion exchanger. In some cases, an ionic liquid may be removed using click chemistry, e.g., where the salt of the ionic liquid, or the ionic liquid itself is engineered to include a chemoselective tag that provides for immobilization or separation from the aqueous sample. In some cases, an ionic liquid may be removed using a photocleavable group, e.g., via removal of a photocleavable ionic liquid or salt thereof from a sample by application of light to photocleave the ionic liquid. Cleavage of the ionic liquid may provide two or more fragments, where some of the fragments produced are more easily extracted or separated from the sample of interest. In certain embodiments, ionic liquids may be removed from an aqueous sample via fluorous affinity interactions of a fluorous salt of the ionic liquid and an ion exchanger with a fluorous affinity substrate. In certain instances, the fluorous salt is removed using fluorous affinity chromatography. In certain instances, the fluorous salt is removed via extraction with a fluorous liquid.

Ionic Liquids

An ionic liquid is a salt in which counterions are poorly coordinated, and which results in the salts being in liquid form below 100° C. The term "ionic liquid" is used in its conventional sense to refer to a salt in liquid state. Ionic liquids of interest are compounds in the liquid state at room temperature that are made of ions or short-lived ion pairs and may alternatively be referred to as liquid electrolytes, ionic melts, ionic fluids, fused salts, liquid salts or ionic glasses. As such, ionic liquids may include salts composed of ion pairs that are in the liquid state at room temperature. In some cases, at least one ion in the ionic salt has a delocalized charge. In some cases, at least one ion in the ionic salt is organic, which prevents the formation of a stable crystal lattice. In some embodiments, the ionic salt includes an organic cation and an inorganic anion. In certain embodiments, the inorganic anion is a chloride. In some embodiments, the ionic salt includes an organic anion and an inorganic cation. In certain embodiments, the inorganic cation is a monovalent metal ion, such as a sodium, potassium or lithium. Any convenient ionic salts may find use in the subject methods and compositions. Ionic salts of interest include, but are not limited to, imidazolium salts, pyridinium salts, pyrrolidinium salts, phosphonium salts, ammonium salts, sulfonium salts, alkylsulfate salts, tosylate salts, methanesulfonate salts, bis(trifluoromethyl-sulfonyl)imide salts, hexafluoro-phosphate salts, and tetrafluoro-borate salts. In some embodiments, the ionic liquid includes a cation selected from the group consisting of sulfonium cations, phosphonium cations, tetraalkyl ammonium cations and pyrazolium cations. In certain embodiments, the ionic liquid is hydrophilic. In some embodiments, the ionic liquid is hydrophobic.

In some embodiments, the ionic liquid includes a cation of Formula (I):

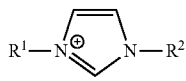

(I)

where each of $R^1$ and $R^2$ is independently hydrogen, alkyl, substituted alkyl, aryl, substituted aryl, arylalkyl, substituted arylalkyl, heteroalkyl, substituted heteroalkyl, heteroaryl, substituted heteroaryl, heteroarylalkyl or substituted heteroarylalkyl.

In some embodiments, the ionic liquid includes a cation of Formula (II):

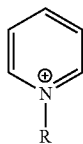

(II)

where R is hydrogen, alkyl, substituted alkyl, aryl, substituted aryl, arylalkyl, substituted arylalkyl, heteroalkyl, substituted heteroalkyl, heteroaryl, substituted heteroaryl, heteroarylalkyl or substituted heteroarylalkyl.

In some embodiments, the ionic liquid includes a cation of Formula (III):

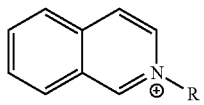

(III)

where R is hydrogen, alkyl, substituted alkyl, aryl, substituted aryl, arylalkyl, substituted arylalkyl, heteroalkyl, substituted heteroalkyl, heteroaryl, substituted heteroaryl, heteroarylalkyl or substituted heteroarylalkyl.

In some embodiments, the ionic liquid includes a cation of Formula (IV):

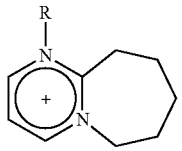

(IV)

where R is hydrogen, alkyl, substituted alkyl, aryl, substituted aryl, arylalkyl, substituted arylalkyl, heteroalkyl, substituted heteroalkyl, heteroaryl, substituted heteroaryl, heteroarylalkyl or substituted heteroarylalkyl.

In some embodiments, the ionic liquid includes a cation of Formula (V):

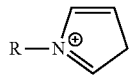

(V)

where R is hydrogen, alkyl, substituted alkyl, aryl, substituted aryl, arylalkyl, substituted arylalkyl, heteroalkyl, substituted heteroalkyl, heteroaryl, substituted heteroaryl, heteroarylalkyl or substituted heteroarylalkyl.

In some embodiments, the ionic liquid includes a cation of Formula (VI):

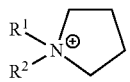

(VI)

where each of $R^1$ and $R^2$ is independently hydrogen, alkyl, substituted alkyl, aryl, substituted aryl, arylalkyl, substituted arylalkyl, heteroalkyl, substituted heteroalkyl, heteroaryl, substituted heteroaryl, heteroarylalkyl or substituted heteroarylalkyl.

In certain embodiments, the ionic liquid includes a cation having Formula (I):

where each of $R^1$ and $R^2$ is independently hydrogen, alkyl, substituted alkyl, aryl, substituted aryl, arylalkyl, substituted arylalkyl, heteroalkyl, substituted heteroalkyl, heteroaryl, substituted heteroaryl, heteroarylalkyl, substituted heteroarylalkyl. In some instances of formula (I), $R^1$ is alkyl or a substituted alkyl and $R^2$ is alkyl or a substituted alkyl. In some instances of formula (I), $R^1$ and $R^2$ are independently selected from methyl, ethyl, propyl, butyl, pentyl, hexyl, heptyl and octyl. In some instances of formula (I), $R^1$ is methyl and $R^2$ is butyl.

Ionic liquids of interest include, but are not limited to 1-butyl-3-methyl-imidazol-3-ium. In certain embodiments, the ionic liquid is a compound selected from the group consisting of 1,2,4-trimethylpyrazolium methylsulfate, methyl-trioctylammonium bis(trifluoromethylsulfonyl)imide, trihexyltetradecylphosphonium bromide and 5-(trifluoromethyl)dibenzothiophenium trifluoromethanesulfonate. In some embodiments, the ionic liquid includes 1-hexyl-3-methyl-imidazolium.

In some embodiments, the ionic liquid includes an anion (e.g., an organic anion), such as an anion selected from the group consisting of a carboxylate, a phosphate ester, a sulfonate, and a borate. Any convenient anions may be utilized in the subject ionic liquids.

In certain embodiments, the ionic liquid is fluorinated. In some instances, the ionic liquid includes a perfluorinated group. Any convenient fluorinated derivatives of ionic liquids may be utilized. In certain embodiments, the fluorinated ionic liquid includes a cation selected from the group consisting of:

a) Formula (I):

where each of R¹ and R² is independently hydrogen, alkyl, perfluoroalkyl, a substituted alkyl, aryl, perfluoroaryl, substituted aryl, arylalkyl, substituted arylalkyl, heteroalkyl, substituted heteroalkyl, heteroaryl, perfluoro substituted heteroaryl, heteroarylalkyl, substituted heteroarylalkyl, or fluorinated or perfluorinated derivatives thereof; or b) Formula (II):

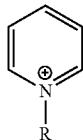

where R is hydrogen, alkyl, perfluoroalkyl, a substituted alkyl, aryl, perfluoroaryl, substituted aryl, arylalkyl, substituted arylalkyl, heteroalkyl, substituted heteroalkyl, heteroaryl, perfluoro substituted heteroaryl, heteroarylalkyl, substituted heteroarylalkyl, or fluorinated or perfluorinated derivatives thereof; or c) Formula (III):

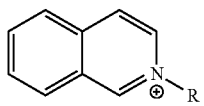

where R is hydrogen, alkyl, perfluoroalkyl, a substituted alkyl, aryl, perfluoroaryl, substituted aryl, arylalkyl, substituted arylalkyl, heteroalkyl, substituted heteroalkyl, heteroaryl, perfluoro substituted heteroaryl, heteroarylalkyl, substituted heteroarylalkyl, or fluorinated or perfluorinated derivatives thereof; or d) Formula (IV):

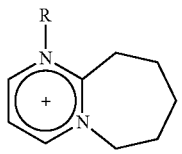

where R is hydrogen, alkyl, perfluoroalkyl, a substituted alkyl, aryl, perfluoroaryl, substituted aryl, arylalkyl, substituted arylalkyl, heteroalkyl, substituted heteroalkyl, heteroaryl, perfluoro substituted heteroaryl, heteroarylalkyl, substituted heteroarylalkyl, or fluorinated or perfluorinated derivatives thereof; or e) Formula (V):

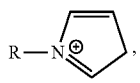

where each of R¹ and R² is independently hydrogen, alkyl, perfluoroalkyl, a substituted alkyl, aryl, perfluoroaryl, substituted aryl, arylalkyl, substituted arylalkyl, heteroalkyl, substituted heteroalkyl, heteroaryl, perfluoro substituted heteroaryl, heteroarylalkyl, substituted heteroarylalkyl, or fluorinated or perfluorinated derivatives thereof; or f) Formula (VI):

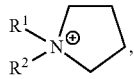

where each of R¹ and R² is independently hydrogen, alkyl, perfluoroalkyl, a substituted alkyl, aryl, perfluoroaryl, substituted aryl, arylalkyl, substituted arylalkyl, heteroalkyl, substituted heteroalkyl, heteroaryl, perfluoro substituted heteroaryl, heteroarylalkyl, substituted heteroarylalkyl, or fluorinated or perfluorinated derivatives thereof.

In certain embodiments, the fluorinated ionic liquid includes a cation having Formula (I):

where each of R¹ and R² is independently hydrogen, alkyl, perfluoroalkyl, a substituted alkyl, aryl, perfluoroaryl, substituted aryl, arylalkyl, substituted arylalkyl, heteroalkyl, substituted heteroalkyl, heteroaryl, perfluoro substituted heteroaryl, heteroarylalkyl, substituted heteroarylalkyl, or fluorinated or perfluorinated derivatives thereof.

In certain embodiments, the ionic liquid includes a cation having Formula (I):

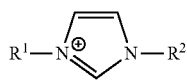

where each of $R^1$ and $R^2$ is independently an alkyl, a substituted alkyl (such as a fluorinated alkyl). In certain instances, $R^1$ and $R^2$ are each independently a perfluorinated alkyl.

In some instances, the ionic liquid includes a fluorinated derivative of any one of the cations of Formulae (I) to (VI), e.g., as described above. In certain embodiments, fluorinated ionic liquids of interest include 1-butyl-3-methyl-imidazol-3-ium, wherein the 1-butyl and 3-methyl substituents are fluorinated.

Reverse Phase Chromatography

Aspects of the method include the use of reverse phase chromatography to adsorb proteins and/or lipids that may be present in the aqueous sample. In some embodiments, the method further includes, contacting the aqueous sample including an ionic liquid with a reverse phase substrate, thereby adsorbing proteins and/or lipids on the reverse phase substrate, if present in the aqueous sample. In some instances, the aqueous sample is a cellular sample that includes an ionic liquid. As such, the cellular sample may be one to which an ionic liquid has been added to lyse the cells and/or quench metabolism of the cells in the sample (e.g., as described herein). In such cases, removal of proteins and/or lipids from the sample ensures metabolism remains quenched, e.g., by removing metabolic enzymes from analytes of interest. In some embodiments, the method further includes lysing cells of a biological sample; and contacting a biological sample with an amount of the ionic liquid sufficient to denature intracellular metabolic enzymes in the biological sample to produce the aqueous sample. The proteins and/or lipids of interest from the sample that are adsorbed on a reverse phase chromatography support and separated from the aqueous sample may be subsequently eluted from the support. In such cases, any convenient analysis of the proteins and/or lipid may be performed, e.g., mass spectroscopic analysis.

Ion Exchanger Composition

In the subject methods, the aqueous sample is subsequently contacted with an ion exchanger composition to produce a composition where the ionic liquid exchanges cations with the ion exchanger composition in a salt metathesis reaction. The term salt "metathesis" reaction is used in its conventional sense to refer to the transposition chemical process involving the exchange of bonds between two ionic species which result in the exchanging of counterions between the two salts. In other words, the subject ionic liquid will undergo a metathesis reaction with the added salt to exchange counterions forming two new distinct salt compounds. This reaction may be represented generally by generic scheme 1 below:

A-B+C-D→A-D+C—B       (Scheme 1)

In some embodiments, the ion exchange composition is a second ionic liquid. For example, in certain embodiments, the ion exchange composition includes lithium bis[(trifluoromethane)sulfonyl]imide (LiNTf$_2$) and the anion exchange with the ionic liquid includes the formation of a new ionic salt having a bis[(trifluoromethane)sulfonyl]imide (NTf$_2$) anion. Any convenient ion exchanger compositions may be utilized in the subject methods. Ion exchanger compositions of interest include those compositions described in U.S. provisional application Ser. No. 62/051,804, U.S. provisional application Ser. No. 62/049,285; and U.S. provisional application Ser. No. 14/205,100, the disclosures of which are incorporated herein by reference.

In some embodiments, the method includes combining an aqueous sample including an ionic liquid with an ion exchange composition including an ion exchanger counterion to produce a solution including a fluorous salt of the ionic liquid. In the fluorous salt, at least one of the ionic liquid and the ion exchanger counterion is fluorinated. As used herein, by "fluorinated" is meant that the group or moiety to which the term refers includes at least one fluorine substituent. In some cases, a fluorinated moiety is perfluorinated. As used here, the term "perfluorinated" refers to an organic group or moiety that includes no C—H covalent bonds and a plurality of fluorinated substitutents. A perfluorinated group may include one or more additional non-fluorine substituents. The ion exchanger composition may include any convenient salt of the ion exchanger counterion. In general terms, the ionic liquid combines with the ion exchanger counterion to produce a fluorous salt that provides for removal of the ionic liquid from the aqueous sample. The ionic liquid and the ion exchanger counterion may be selected to provide for a salt having a desired property. In certain embodiments, the salt is a fluorous salt that provides for extraction of the salt from the aqueous sample using a fluorous affinity substrate or a fluorous solvent. In such cases, either the ionic liquid or the ion exchanger or both may be fluorinated in order to provide a fluorous salt that has affinity for a fluorous affinity substrate and/or high solubility in a fluorous solvent.

Any convenient fluorinated (e.g., perfluorinated) counterions may be utilized in the subject ion exchange compositions. As used herein, the term "fluorinated counterion" refers to a counterion of the ion exchanger composition capable of forming a salt with an ionic liquid of interest, where the counterion is fluorinated. As such, the term fluorinated when used herein in the context of a "fluorinated counterion" refers to both fluorinated and perfluorinated chemical groups and is meant to encompass any organic ions that have two or more fluorine atoms, such as 3 or more, 4 or more, 5 or more, 6 or more, 7 or more, 8 or more, 9 or more, or even 10 or more fluorine atoms. In some cases, the "fluorinated counterion" includes a perfluoro group where all the hydrogens attached to carbon atoms of the group are replaced with fluorine atoms. As such, the "fluorinated counterion" may include one or more hydrocarbons (i.e., C—H containing groups).

In some embodiments, the ion exchanger counterion is described by the formula (VII):

$$Z^1\text{-}L^1\text{-}A\text{-}(\text{-}L^2\text{-}Z^2)_n$$

wherein:

$Z^1$ is a perfluoroalkyl, an alkyl, a substituted alkyl, a perfluoroaryl, an aryl or a substituted aryl;

n is 0, 1, 2 or 3;

each $Z^2$, if present, is independently selected from the group consisting of a perfluoroalkyl, a perfluoroaryl, an alkyl, a substituted alkyl, an aryl and a substituted aryl;

A is a charged moiety capable of acting as a counterion to the ionic liquid; and $L^1$ and $L^2$ are independently a covalent bond or a linker.

In certain embodiments, in formula (VII), $Z^1$ is a perfluoroalkyl, or a fluorinated alkyl. In certain embodiments, in formula (VII), $Z^1$ is a perfluoroaryl, or a fluorinated aryl.

In certain embodiments, in formula (VII), each $Z^2$ is a perfluoroalkyl, or a fluorinated alkyl. In certain embodiments, in formula (VII), each $Z^2$ is a perfluoroaryl, or a fluorinated aryl.

In certain embodiments, in formula (VII), n is 0. In certain embodiments, in formula (VII), n is 1. In certain embodiments, in formula (VII), n is 2. In certain embodiments, in formula (VII), n is 3.

In certain embodiments, in formula (VII), $L^1$ and each $L^2$ is an alkyl (e.g., a linear alkyl linker, such as —CH$_2$—, —CH$_2$CH$_2$— or —(CH$_2$)$_m$— where m is an integer from 1 to 12, e.g., m is an integer from 1 to 6).

In certain embodiments, in formula (VII), A is an organic anion selected from a sulfonimidate, a sulfonate, a carboxylate, a phosphate and a borate.

In certain embodiments, in formula (VII), when n=1, A is —SO$_2$N($^-$)SO$_2$—. In certain embodiments, in formula (VII), when n=0, A is —SO$_2$NH($^-$).

In some embodiments, the perfluorous counterion is described by formula (VIII):

$$Z^1\text{-}L^1\text{-}A \qquad\qquad (VIII)$$

wherein $Z^1$, $L^1$ and A are as defined in for Formula (VII).

In certain embodiments, in formula (VIII), A is an organic anion selected from a sulfonimidate, a sulfonate, a carboxylate, a phosphate and a borate.

In certain embodiments, in formulae (VII) and (VIII), $L^1$ and each $L^2$ are independently a C$_1$-C$_6$ alkyl linker or a covalent bond. In certain embodiments, in formulae (VII) and (VIII), $L^1$ and each $L^2$ are independently selected from —CH$_2$CH$_2$— or a covalent bond.

In certain embodiments, in formulae (VII) and (VIII), $Z^1$ and $Z^2$ are each independently a perfluoroalkyl group (e.g., comprising 4 or more fluorinated carbon atoms). In certain embodiments, in formulae (VII) and (VIII), $Z^1$ and each $Z^2$ comprise together a combined total of 8 or more fluorinated carbon atoms (e.g., 10 or more, 12 or more, 14 or more, 16 or more, 18 or more or even 20 or more fluorinated carbon atoms).

In some embodiments, the ion exchanger counterion is an ion exchanger counterion described by the formula (IX):

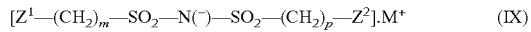

where: $Z^1$ and $Z^2$ are independently a perfluoroalkyl, an alkyl, a substituted alkyl, a perfluoroaryl, an aryl, or a substituted aryl, wherein $Z^1$ and $Z^2$ include together a combined total of 8 or more fluorinated (e.g., perfluorinated) carbon atoms (e.g., 9 or more, 10 or more, 11 or more, 12 or more, 13 or more, 14 or more, 15 or more, 16 or more, 17 or more, 18 or more, 19 or more, 20 or more, 30 or more or 40 or more fluorinated carbon atoms); m and p are independently 0, 1 or 2; and $M^+$ is a cation.

In certain embodiments of formula (IX), $Z^1$ and $Z^2$ are the same. In certain embodiments of formula (IX), $Z^1$ and $Z^2$ are the different. In certain embodiments of formula (IX), $Z^1$ and $Z^2$ are each a fluorinated or perfluorinated group. In certain embodiments of formula (IX), at least one of $Z^1$ and $Z^2$ is a fluorinated or perfluorinated group. In certain embodiments of formula (IX), $Z^1$ and $Z^2$ are each a perfluoroalkyl. In certain embodiments of formula (IX), $Z^1$ and $Z^2$ are each perfluorobutyl. In certain embodiments of formula (IX), $Z^1$ and $Z^2$ are each perfluoropentyl. In certain embodiments of formula (IX), $Z^1$ and $Z^2$ are each perfluorohexyl. In certain embodiments of formula (IX), $Z^1$ and $Z^2$ are each a perfluoroheptyl. In certain embodiments of formula (IX), $Z^1$ and $Z^2$ are each a perfluorooctyl. In certain embodiments of formula (IX), $Z^1$ and $Z^2$ are each a perfluoroaryl. In certain embodiments of formula (IX), $Z^1$ and $Z^2$ include together a combined total of 10 or more perfluorinated carbon atoms. In certain embodiments of formula (IX), $Z^1$ and $Z^2$ include together a combined total of 12 or more perfluorinated carbon atoms. In certain embodiments of formula (IX), m and p are each 0. In certain embodiments of formula (IX), m+p=1. In certain embodiments of formula (IX), m+p=2. In certain embodiments of formula (VII), m+p=3. In certain embodiments of formula (IX), m+p=4. In certain embodiments of formula (IX), $M^+$ is lithium. In certain embodiments of formula (IX), $M^+$ is potassium. In certain embodiments of formula (IX), $M^+$ is sodium. In certain embodiments of formula (IX), $M^+$ is rubidium. In certain embodiments of formula (IX), $M^+$ is silver.

In certain instances, the ion exchange composition includes a salt having an anion selected from the group consisting of boron tetrafluoride, bis-(2,4,4-trimethylpentyl) phosphinate, bis-(trifluoromethyl)imide, bis[(trifluoromethane)sulfonyl]imide, bis-(trifluoromethylsulfonyl) methane, bis-biphenyldiolatoborate, bis-malonatoborate, bis-oxalatoborate, bis-(pentafluoroethyl)phosphinate, bis-salicylatoborate, bromine, butylsulfate, chloride, perchlorate, decanoate, dicyanamide, ethylsulfate, iodide, methylsulfate, octylsulfate, hexafluorophosphate, tetracyanoborate, toluene-4-sulfonate, trifluoromethane-sulfonate, tris-(nonafluorobutyl)-trifluorophosphate and tris-(pentafluoroethyl) trifluorophosphate. In some embodiments, the ion exchanger counterion is bisnonafluoro-1-butanesulfonimidate. In some embodiments, the ion exchanger counterion is bis((perfluorohexyl)sulfonyl)imide.

In some embodiments, the ion exchanger composition includes a salt of the ion exchanger counterion selected from silver, lithium, sodium, rubidium and potassium. In some embodiments, the ion exchanger composition includes a silver salt of the ion exchanger counterion. In general terms, the ion exchanger composition may include a salt of a metal cation and an ion exchanger counterion that is an anion. In the subject methods the ion exchanger counterion forms a new fluorous salt with the ionic liquid, and the metal cation is free to form another salt with any convenient anions that are present in the sample. The metal cation may be selected to provide for any desirable property, such as facile removal via an insoluble halide salt. In some embodiments, the method further includes producing an insoluble silver salt, such as silver chloride. In some instances, the method further includes separating an insoluble silver salt from the aqueous sample, where the silver cation of the salt is derived from the ion exchanger composition. Any convenient methods for separating a solid from a liquid may be utilized, including but not limited to, centrifugation, filtration, decanting, and the like.

Fluorous Salt

Also provided is a composition including a fluorous salt of an ionic liquid and a fluorous solvent. In some embodiments of the composition, the fluorous salt of the ionic liquid includes a fluorinated ion exchanger counterion (e.g., as described herein) and an ionic liquid cation (e.g., as described herein). In some embodiments of the composition, the fluorous salt includes a fluorinated ion exchanger counterion of formula (VII): $[Z^1—(CH_2)_m—SO_2—N(^-)—SO_2—(CH_2)_p—Z^2].M^+$ (VII) where: $Z^1$, $Z^2$, m and p are as defined above; and $M^+$ is a cation selected from the group consisting of:

a) Formula (I):

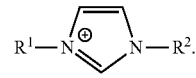

wherein each of $R^1$ and $R^2$ is independently hydrogen, alkyl, substituted alkyl, aryl, substituted aryl, arylalkyl, substituted arylalkyl, heteroalkyl, substituted heteroalkyl, heteroaryl, substituted heteroaryl, heteroarylalkyl, substituted heteroarylalkyl;

b) Formula (II):

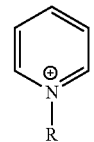

wherein R is hydrogen, alkyl, substituted alkyl, aryl, substituted aryl, arylalkyl, substituted arylalkyl, heteroalkyl, substituted heteroalkyl, heteroaryl, substituted heteroaryl, heteroarylalkyl, substituted heteroarylalkyl;

c) Formula (III):

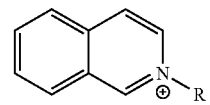

wherein R is hydrogen, alkyl, substituted alkyl, aryl, substituted aryl, arylalkyl, substituted arylalkyl, heteroalkyl, substituted heteroalkyl, heteroaryl, substituted heteroaryl, heteroarylalkyl, substituted heteroarylalkyl;

d) Formula (IV):

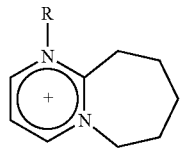

wherein R is hydrogen, alkyl, substituted alkyl, aryl, substituted aryl, arylalkyl, substituted arylalkyl, heteroalkyl, substituted heteroalkyl, heteroaryl, substituted heteroaryl, heteroarylalkyl, substituted heteroarylalkyl;

e) Formula (V):

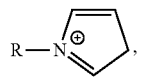

wherein each of $R^1$ and $R^2$ is independently hydrogen, alkyl, substituted alkyl, aryl, substituted aryl, arylalkyl, substituted arylalkyl, heteroalkyl, substituted heteroalkyl, heteroaryl, substituted heteroaryl, heteroarylalkyl, substituted heteroarylalkyl; and f) Formula (VI):

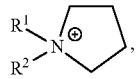

wherein each of $R^1$ and $R^2$ is independently hydrogen, alkyl, substituted alkyl, aryl, substituted aryl, arylalkyl, substituted arylalkyl, heteroalkyl, substituted heteroalkyl, heteroaryl, substituted heteroaryl, heteroarylalkyl, substituted heteroarylalkyl. In some embodiments of the composition, the cation is 1-hexyl-3-methyl-imidazolium. In some embodiments of the composition, the fluorinated ion exchanger counterion is bis((perfluorohexyl)sulfonyl)imide.

In some embodiments, the ionic liquid of the fluorous salt is fluorinated (e.g., as described herein). Any convenient fluorinated ionic liquid cations (e.g., as described herein) may be utilized in the subject methods to produce a fluorous salt. In certain cases, both the ionic liquid cation and the ion exchanger counter ion of the fluorous salt are fluorinated (e.g., as described herein). In some embodiments, the ionic liquid is not fluorinated.

In some instances, the ionic liquid exchanges anions with the ion exchange composition to form a new salt having an anion that is selected from boron tetrafluoride, bis-(2,4,4-trimethylpentyl)phosphinate, bis-(trifluoromethyl)imide, bis[(trifluoromethane)sulfonyl]imide, bis-(trifluoromethylsulfonyl) methane, bis-biphenyldiolatoborate, bis-malonatoborate, bis-oxalatoborate, bis-(pentafluoroethyl) phosphinate, bis-salicylatoborate, bromine, butylsulfate, chloride, perchlorate, decanoate, dicyanamide, ethylsulfate, iodide, methylsulfate, octylsulfate, hexafluorophosphate, tetracyanoborate, toluene-4-sulfonate, trifluoromethane-sulfonate, tris-(nonafluorobutyl)-trifluorophosphate and tris-(pentafluoroethyl)trifluorophosphate.

Fluorous Affinity Material

The subject methods include contacting the aqueous solution that includes the fluorous salt of the ionic liquid with a fluorous affinity material. As used herein the term "fluorous affinity material" refers to a material, such as a support or a liquid that has greater affinity for a fluorinated moiety of interest than for a non-fluorinated moiety. In some instances, the "fluorous affinity material" takes advantage of the heightened affinity that fluorinated moieties, such as perfluorinated moieties, have for each other. The fluorous affinity material is capable of removing the fluorous salt from the aqueous solution. Any convenient fluorous affinity materials may be utilized in the subject methods to remove the fluorous salt from the aqueous solution. Fluorous affinity materials of interest include, but are not limited to, fluorous affinity chromatography supports such as FLUORO-PAK™ and FLUORO-PAK™ II columns (Berry & Associates) or fluorous silica, and fluorous solvents such as perfluorocarbons (PFCs) and hydrofluoroethers (HFEs). Perfluorocarbons of interest include, but are not limited to, perfluorohexane, perfluoromethylcyclohexane and perfluorodecalin. Hydrofluoroethers of interest include, but are not limited to, nonafluorobutyl methyl ether (e.g., HFE-7100). In some embodiments, the fluorous solvent is methoxyperfluorobutane.

Any convenient fluorous affinity methods and configurations of fluorous affinity materials may be utilized in the removal of the fluorous salt from the aqueous sample. Methods of interest include, but are not limited to, solid phase extraction and liquid phase extraction, such as those methods described by Pearson et al., "Fluorous Affinity Purification of Oligonucleotides", J. Org. Chem., 2005, 70 (18), pp 7114-7122; US20060178507; Hayama et al., Journal of Pharmaceutical and Biomedical Analysis, Volume 101, December 2014, Pages 151-160; Heitzman et al., "Fluorous ionic liquids as solvents for the liquid-liquid extraction of metal ions by macrocyclic polyethers", Talanta, Volume 69, Issue 2, 15 Apr. 2006, Pages 527-531; and Dandapani, S., "Recent applications of fluorous separation methods in organic and bioorganic chemistry", QSAR & Combinatorial Science 2006, 25, (8-9), 681-688.

After the fluorous salt has been removed from the aqueous sample, e.g., via solid-phase or liquid phase extraction, the remaining material of the aqueous sample may be referred to as an aqueous eluate. In some embodiments of the method, the fluorous affinity material is an immiscible fluorous solvent that extracts the fluorous salt from the aqueous solution to produce the aqueous eluate. In such cases, the aqueous eluate is not miscible with the fluorous solvent and may be easily separated from the fluorous solvent, e.g., by decanting. In some embodiments of the method, the fluorous affinity material is a fluorous affinity chromatography support that adsorbs the fluorous salt from the solution to produce the aqueous eluate. In such cases, the aqueous eluate may be the solution that passes through the column and is collected.

The aqueous eluate may be further analyzed using any convenient methods. Methods of analysis of interest include, but are not limited to, mass spectrometry (MS), gas chromatography (GC), GC-MS, High performance liquid chromatography (HPLC), HPLC-MS, capillary electrophoresis (CE), nuclear magnetic resonance (NMR), infrared spectroscopy, UV-vis spectroscopy, colorimetry, and the like. The aqueous eluate may include any convenient analytes of interest and the subject methods may provide for an improved detection and/or analysis of those analytes. In some cases, the ionic liquid is a contaminant that prevents sensitive detection and analysis of the analytes in the sample. For example, the ionic liquid may contaminate a mass spectrometer during sample analysis, e.g., by suppressing ion counts of an analyte of interest. In some embodiments, the method further includes analyzing the aqueous eluate by mass spectrometry. In some cases, the removal of the ionic liquid from the aqueous sample leads to increased sensitivity of detection and/or analysis of an analyte by mass spectrometry.

As described above, methods of the present disclosure may include analyzing the analyte containing compositions using liquid chromatography-mass spectrometry systems. For example, the apparatus may include analytical separation device such as a liquid chromatograph (LC), including a high performance liquid chromatograph (HPLC), a micro- or nano-liquid chromatograph or an ultra-high pressure liquid chromatograph (UHPLC) device, a capillary electrophoresis (CE), or a capillary electrophoresis chromatograph (CEC) apparatus. However, any manual or automated injection or dispensing pump system may be used. For instance, a the subject sample may be applied to the LC-MS system by employing a nano- or micropump in certain embodiments.

Mass spectrometer systems for use in the subject methods may be any convenient mass spectrometry system, which in general contains an ion source for ionizing a sample, a mass analyzer for separating ions, and a detector that detects the ions. In certain cases, the mass spectrometer may be a so-called "tandem" mass spectrometer that is capable of isolating precursor ions, fragmenting the precursor ions, and analyzing the fragmented precursor ions. Such systems are well known in the art (see, e.g., U.S. Pat. Nos. 7,534,996, 7,531,793, 7,507,953, 7,145,133, 7,229,834 and 6,924,478) and may be implemented in a variety of configurations. In certain embodiments, tandem mass spectrometry may be done using individual mass analyzers that are separated in space or, in certain cases, using a single mass spectrometer in which the different selection steps are separated in time. Tandem MS "in space" involves the physical separation of the instrument components (QqQ or QTOF) whereas a tandem MS "in time" involves the use of an ion trap.

An example mass spectrometer system may contain an ion source containing an ionization device, a mass analyzer and a detector. As is conventional in the art, the ion source and the mass analyzer are separated by one or more intermediate vacuum chambers into which ions are transferred from the ion source via, e.g., a transfer capillary or the like. Also as is conventional in the art, the intermediate vacuum chamber may also contain a skimmer to enrich analyte ions (relative to solvent ions and gas) contained in the ion beam exiting the transfer capillary prior to its entry into the ion transfer optics (e.g., an ion guide, or the like) leading to a mass analyzer in high vacuum.

The ion source may rely on any type of ionization method, including but not limited to electrospray ionization (ESI), atmospheric pressure chemical ionization (APCI), electron impact (EI), atmospheric pressure photoionization (APPI), matrix-assisted laser desorption ionization (MALDI) or inductively coupled plasma (ICP) ionization, for example, or any combination thereof (to provide a so-called "multi-mode" ionization source). In one embodiment, the precursor ions may be made by EI, ESI or MALDI, and a selected precursor ion may be fragmented by collision or using photons to produce product ions that are subsequently analyzed.

Likewise, any of a variety of different mass analyzers may be employed, including time of flight (TOF), Fourier transform ion cyclotron resonance (FTICR), ion trap, quadrupole or double focusing magnetic electric sector mass analyzers, or any hybrid thereof. In one embodiment, the mass analyzer may be a sector, transmission quadrupole, or time-of-flight mass analyzer.

Methods for Preparation of a Cellular Sample for Analysis

Also provided is a method for preparation of a cellular sample for analysis. In some cases, the method for preparation of a cellular sample for analysis includes extracting and purifying compounds from a biological sample including cells. The phrase "extracting and purifying" is used herein in its conventional sense to refer to isolating desired compounds (e.g., metabolites) from a plurality of components in a biological sample having cells. In some embodiments, the method further includes lysing cells of a biological sample by contacting a biological sample with an amount of the ionic liquid sufficient to denature intracellular metabolic enzymes in the biological sample to produce the aqueous sample.

In certain embodiments, compounds extracted by the subject methods are metabolites. The term "metabolites" is used herein its conventional sense to refer to one or more compounds found which are the substrates or products of metabolic process which occur within a cell. As such, metabolites may include substrates or products which are produced by metabolic processes including, but not limited to glycolysis, tricarboxylic acid cycle (i.e., TCA cycle, Krebs cycle), reductive pentose phosphate cycle (i.e., Calvin cycle), glycogen metabolism, pentose phosphate pathway, among other metabolic processes. Accordingly, metabolites of interest may include but are not limited to glucose, glucose-6-phosphate, fructose-6-phosphate, fructose-1,6-phosphate, glyceraldehyde 3-phosphate, dihydroxyacetone phosphate, 1,3-bisphosphoglycerate, 3-phosphoglycerate, 2-phosphoglycerate, phosphoenolpyruvate, pyruvate, acetyl CoA, citrate, cis-aconitate, d-isocitrate, α-ketoglutarate, succinyl CoA, succinate, fumarate, malate, oxaloacetate, ribulose 1,5-bisphosphate, 3-phosphoglycerate, 1,3-bisphosphoglycerate, glyceraldehyde 3-phosphate, ribulose-5-phosphate, ethanol, acetylaldehyde, pyruvic acid, 6-phosphogluconolactone, 6-phosphogluconate, ribose-5-phosphate, xylulose-5-phosphate, sedoheptulose 7-phosphate, erythrose 4-phosphate, among other metabolites.

Aspects of the method include lysing cells of a biological sample and contacting the biological sample with an amount of ionic liquid sufficient to denature intracellular metabolic enzymes in the biological sample. By "lyse" cells is meant that the cells are ruptured or broken open such that the internal contents of the cells, including metabolic enzymes are released into the surrounding medium (e.g., ionic liquid). In some embodiments, cell lysis may further include lysis of cellular organelles, for example the nucleus, mitochondria, ribosomes, chloroplasts, lysosomes, vacuoles, Golgi apparatus, centrioles, etc. such that the contents of the cellular organelles are also released into the surrounding medium.

In some embodiments, lysing the cells of a biological sample is performed by contacting the cells of the biological sample with a lysing agent (e.g., an ionic liquid, as described herein). The lysing agent may be any suitable lysing agent so long as it is sufficient to break open the cells where that the internal contents of the cell are released into the surrounding medium. The lysing agent may be contacted with the biological sample having the cells at the same time (i.e., simultaneously) as contacting the biological sample having cells with ionic liquid. In some cases, the lysing agent may be contacted with the biological sample sufficient to break open the cells before contacting the sample with the ionic liquid. In other words, in these embodiments, the biological sample having cells that is contacted with the ionic liquid includes cells which have been previously broken open by one or more lysing agents. In certain embodiments, the ionic liquid functions as the lysing agent and contacting the biological sample having cells with the ionic liquid is sufficient to lyse the cells of the sample and denature intracellular metabolic enzymes without the need for an additional lysing agent. In some embodiments, the method includes contacting a biological sample having cells with an amount of ionic liquid composition (e.g., as described herein) sufficient to lyse the cells and denature intracellular metabolic enzymes in the biological sample. In certain instances of the method, the ionic liquid composition is an aqueous composition including 30% or more of an ionic liquid by weight, such as 35% or more by weight, 40% or more by weight, 45% or more by weight, 50% or more by weight, 55% or more by weight, 60% or more by weight, 65% or more by weight, 70% or more by weight, 75% or more by weight, 80% or more of an ionic liquid by weight, or even more.

As described in greater detail below, intracellular enzymes are denatured by contacting with the ionic liquid. The term "denature" is used in its conventional sense to mean that the structural conformation of the subject proteins or enzymes is destabilized or disrupted, in certain embodiments the proteins or enzymes losing quaternary, tertiary and secondary structure that is otherwise present in its native state. Protein denaturation by the ionic liquid includes quaternary denaturation where protein sub-units are dissociated or the spatial arrangement of protein subunits is disrupted. Protein denaturation by ionic liquids may further include tertiary structure denaturation which includes the disruption of covalent interactions between amino acid side chains (such as disulfide bridges between cysteine groups), non-covalent dipole-dipole interactions between polar amino acid side chains and surrounding media, Van der Waals interactions (e.g., induced dipole moments) between non-polar amino acid side chains. Protein denaturation by ionic liquids may further include secondary structure denaturation where the proteins or enzymes lose all regular repeating patterns such as alpha-helices and beta-pleated sheets and may adopt a random-coil type configuration. In some embodiments, the biological sample having cells is contacted at room temperature (i.e., about 20° C. or 68° F. or 293K).

Where compounds extracted and purified by the subject methods include metabolites, ionic liquids of interest include those sufficient to destabilize, disrupt or denature metabolic enzymes. Metabolic enzymes of interest include, but are not limited to those employed in the metabolic processes discussed above, such as metabolic enzymes in glycolysis, tricarboxylic acid cycle (i.e., TCA cycle, Krebs cycle), reductive pentose phosphate cycle (i.e., Calvin cycle), glycogen metabolism, the pentose phosphate pathway, among other metabolic processes. For example, metabolic enzymes of interest include, but are not limited to: hexokinase, phosphoglucose isomerase, phosphofructokinase, fructose bisphosphate aldolase, triose phosphate isomerase, glyceraldehyde phosphate dehydrogenase, phophoglycerate kinase, phosphoglycerate mutase, enolase, pyruvate kinase, pyruvate dehydrogenase, citrate synthase, aconitase, isocitrate dehydrogenase, α-ketoglutarate dehydrogenase, succinyl-CoA synthetase, succinic dehydrogenase, fumarase, malate dehydrogenase, pyruvate carboxylase, ribulose-1,5-bisphophate carboxylase oxygenase, glyceraldehyde 3-phosphate dehydrogenase, phosphopentose epimerase, phosphoribulokinase, glucose-6-phosphate dehydrogenase, gluconolactonase, 6-phosphogluconate dehydrogenase, ribulose-5-phosphate isomerase, ribulose-5-phosphate 3-epimerase, transaldolase, transketolase, among other metabolic pathway enzymes.

Contacting the biological sample having cells with the ionic liquid may include mixing the cells in the ionic liquid. Any convenient method may be employed to stir the biological sample having cells with the ionic liquid, so long as the cells are sufficiently mixed throughout and in contact with the ionic liquid. Mixing may include, for example stirring with a magnetic stir bar or manually stirred using any convenient stirring apparatus. Alternatively, the biological sample in the ionic liquid may be stirred by vortexing the contacted sample, shaking the contacted sample such as with a mechanical shaker or shaking may be manually performed (i.e., by hand). In some instances, mixing the biological sample having cells with the ionic liquid includes sonicating the contacted composition.

As described above, methods include contacting a biological sample having cells with an ionic liquid. As noted above, ionic liquids of interest destabilize, disrupt or denature enzyme structure. Any convenient ionic liquid may be employed in the subject methods so long as the ionic liquid destabilizes, disrupts and/or denatures enzyme structure.

Contacting the biological sample having cells with an ionic liquid lyses the cells, releasing the cellular components into the ionic liquid and denatures the metabolic enzymes found within the cells. As such, contacting the biological sample having cells according to the subject methods quenches metabolic processes of the cell upon contact/mixing with the ionic liquid. By "quenches metabolic processes" is meant that metabolic processes which occur in the native cell are stopped by lysis and denaturation. As such, in practicing the subject methods, 95% or more of metabolic process in the cell may be quenched after contacting the biological sample with the ionic liquid, such as 97% or more, 99% or more, 99.5% or more, or 99.9% or more, and including all of the metabolic processes mediated by enzymes which are quenched by lysis and denaturation of metabolic enzymes by contacting with the ionic liquids.

In some instances of the method, reverse phase chromatography is used to adsorb proteins and/or lipids that may be present in the aqueous cellular sample. In some embodiments, the method further includes contacting the aqueous cellular sample including an ionic liquid with a reverse phase substrate, thereby adsorbing proteins and/or lipids on the reverse phase substrate. As such, the cellular sample may be one to which an ionic liquid has been added to lyse the cells and/or quench metabolism of the cells in the sample. In such cases, removal of proteins and/or lipids from the sample ensures metabolism of the cell remains quenched in the aqueous sample, e.g., by removing metabolic enzymes from analytes of interest.

In some embodiments, after contacting the biological sample with the ionic liquid, the cellular sample is mixed with an organic solvent. In certain embodiments, the organic solvent may be added to the ionic liquid cellular sample to form an ionic liquid cellular sample-organic solvent two phase composition. By "two phase composition" is meant that the ionic liquid cellular sample is not miscible with the organic solvent and forms two distinct layers. As such, in these embodiments, the organic solvent and ionic liquids are not miscible. For example, where the ionic liquid is hydrophilic, the organic solvent may be hydrophobic. Likewise, where the ionic liquid is hydrophobic, the organic solvent may be hydrophilic. In certain embodiments where a two-phase composition is formed, the organic liquid is denser than the ionic liquid. In other words, after addition of the organic solvent to the ionic liquid, the organic phase is positioned at the bottom of the two-phase composition and the ionic liquid cellular sample phase is positioned on top.

In some embodiments, the organic liquid mixed with the ionic liquid cellular sample is a hydrophobic or non-polar organic solvent. Hydrophobic or non-polar organic solvents of interest include, but are not limited to, fluorous solvents, pentane, hexane, heptane, octane, diethyl ether, and chloroform. Where a hydrophobic or non-polar organic solvent is employed, non-polar and hydrophobic cellular components may be extracted into the organic solvent layer. As such, the hydrophobic cellular components (e.g., lipids, nonpolar membrane components, etc.) from the ionic liquid cellular sample are extracted into the organic phase of the two phase composition.

In certain embodiments, a dispersed microdroplet composition is produced after mixing an organic liquid with the ionic liquid cellular sample. The term "microdroplet" is used in its conventional sense to refer to aggregates of the ionic liquid cellular sample composition within the organic solvent medium having dimensions ranging from 0.001 μm to 1000 μm, such as 0.01 μm to 100 μm, such as 0.1 μm to 10 μm and including 1 μm. By forming the microdroplets, the surface area of the ionic liquid cellular sample is increased, where in certain instances the hydrophobic components in the ionic liquid cellular sample are extracted into the organic solvent medium. Likewise, by forming a dispersed microdroplet composition, the proteins and enzymes denatured by contacting with the ionic liquid precipitate. In some case, remaining in the ionic liquid phase are the subject compounds, e.g., metabolites. In certain cases, the subject compounds, e.g., metabolites, are dissolved in the aqueous phase.

Microdroplet dispersions may be formed using any convenient protocol, so long as the ionic liquid cellular sample-organic solvent composition is agitated sufficiently to form dispersed microdroplets of ionic liquid cellular sample in the organic solvent medium. In certain embodiments, agitation may result in turbid solutions having a plurality of microdroplets homogeneously dispersed throughout the organic solvent. Agitation may include, but is not limited to, vortexing the composition, sonicating the composition, shaking the composition either manually (i.e., by hand) or mechanically (i.e., by a mechanically or electrically powered shaking device), and rapidly stirring the composition manually, among other agitating protocols. Agitation may be performed for any amount of time, so long as agitation is sufficient to produce the desired microdroplet dispersions. As such, agitation may be performed for one second or longer, such as for two seconds or longer, such as for 5 seconds or longer, such as for 10 seconds or longer, for 30 seconds or longer, for 1 minute or longer, for 5 minutes or longer, or for 10 minutes or longer and including agitation for 30 minutes or longer.

In certain embodiments, a dispersant is not added to the composition to produce the microdroplet dispersions. As such, in these embodiments no additional compounds are added to the composition in order to create the microdroplet dispersions other than agitation of the sample.

In some embodiments of the subject methods, the dispersed microdroplet composition may be subsequently contacted with an ion exchanger composition (e.g., as described herein) to produce an ionic liquid-organic solvent two phase composition where the ionic liquid exchanges cations with the ion exchange composition in a salt metathesis reaction.

In embodiments of the invention, the addition of the ion exchanger composition to the dispersed microdroplet composition is sufficient to form an ionic liquid cellular sample-organic solvent two phase composition. As noted above, the two phase composition includes an ionic liquid composition that is not miscible with the organic solvent and thus, forms two distinct layers. By contacting the dispersed microdroplet composition with the ion exchange composition, the organic layer and ionic liquid layers can be separated. In certain embodiments, the newly formed ionic liquid with exchanged anion is denser than the organic solvent layer. In some cases, after addition of the ion exchange composition to the dispersed microdroplet composition, the organic solvent phase is positioned at the top of the two-phase composition and the ionic liquid phase is positioned on the bottom.

After formation of distinct layers in an ionic liquid-organic solvent two-phase composition, the ionic liquid may be separated from the organic solvent. The ionic liquid may be separated from the organic layer by any convenient protocol, including but not limited pouring off the organic solvent, aspirating to separate the ionic liquid from the organic solvent (e.g., using either a manual, mechanically controlled, hydraulically controlled or electrically controlled pipet) or by evaporation of the organic solvent (e.g., vacuum evaporation, by bubbling inert gas through the organic phase).

Methods of the present disclosure may further include separating the target compounds (e.g., metabolites) extracted from the biological sample cells from the ionic liquid, such as for example by microextraction. Microextraction protocols of interest may be any convenient microextraction so long as the protocol is sufficient to extract the target metabolites from the ionic liquids. For example, microextraction may include solid phase chromatography. In certain embodiments, solid phase chromatography includes, but is not limited to ion exchange chromatography, liquid chromatography employing a reverse phase stationary column, among other chromatography protocols.

In some embodiments, separating the metabolites from the ionic liquid further includes analysis of the separated metabolites. By analyzed is meant characterizing the chemical composition of the separated metabolites, including but not limited to the amount and types of compounds in the extracted metabolites as well as any impurities present. Chemical analysis may be conducted using any convenient protocol, such as for example by mass spectrometry, infrared spectroscopy, UV-vis spectroscopy, colorimetry and nuclear magnetic resonance spectroscopy. In certain embodiments, chemical analysis is conducted by gas chromatography-mass spectrometry. In other embodiments, chemical analysis is conducted by liquid chromatography-mass spectrometry.

Ionic liquids are suitable for denaturing proteins and have been used for the extraction of small molecules and DNA. Using an ionic liquid, the entire cellular contents of a biological sample can be solubilized and denatured. By denaturing the proteins, the degradation of DNA and RNA can be significantly reduced. In one embodiment, an ionic liquid can be used to solubilize the entire contents of a biological sample, denature proteins, DNA, and RNA, and separate each individual component from the mixture.

The denaturation process can be instantaneous when a large amount of ionic liquid is introduced to the sample (e.g., at least 2×, at least 5× or at least 10×, by volume). After addition of the ionic liquid, proteins and/or lipids can be removed from the sample, e.g., via an amine reactive moiety that is attached to a solid phase or by reverse phase chromatography. By removing the protein and/or lipids from the sample, the remaining components may be much less susceptible to degradation. In certain cases, a cleavable linker may be attached to the solid phase so that the proteins can be released from the solid phase and later analyzed by mass spectrometry.

In some embodiments, the method includes combining an ionic liquid with a sample and removing the protein and/or lipid from the sample using a reverse phase chromatography support to produce an aqueous sample. In certain cases, the protein may be released from the support and analyzed. Following the optional removal of the proteins and/or lipids, an ion-exchange reaction can be induced by adding an ion exchanger composition (e.g., as described herein).

In some instances, the method includes combining the aqueous sample either sequentially or simultaneously with: (i) an ion exchanger composition comprising a fluorinated ion exchanger counterion to produce a fluorous salt of the ionic liquid; and (ii) an immiscible fluorous solvent. The ion exchanger composition and the fluorous solvent may be added to the aqueous sample in any convenient order and using any convenient method. The fluorous solvent is not miscible with the aqueous sample and forms a separate liquid phase into which the fluorous salt of the ionic liquid dissolves. The partition coefficient of the fluorous salt in the aqueous sample versus the fluorous solvent may be selected so as to provide for a desired level of extraction of the ionic liquid from the aqueous sample.

After formation of distinct layers in an aqueous sample-fluorous solvent two-phase composition, the ionic liquid may be separated by any convenient protocol, including but not limited pouring off the fluorous solvent, aspirating to separate the aqueous eluate from the fluorous solvent (e.g., using either a manual, mechanically controlled, hydraulically controlled or electrically controlled pipet). In some instances, the method further includes collecting the aqueous phase of the two phase system to produce an aqueous eluate.

As such, the fluorous salt is extracted from the aqueous sample into the fluorous affinity liquid to produce an aqueous eluate of the remaining material of the aqueous cellular sample. The steps of this extraction process may be repeated one or more times, such as two or more, 3 or more, 4 or more or 5 or more times, as desired to remove any remaining ionic liquid from the aqueous sample. Any convenient number of extractions may be performed as necessary to ensure that a desired level of fluorous salt is achieved in the resulting aqueous eluate. In certain embodiments, the aqueous eluate that is produced after liquid phase extraction may be further contacted with a solid phase fluorous affinity support, thereby absorbing residual fluorous salt of the ionic liquid from the aqueous eluate, and producing an aqueous eluate substantially free from ionic liquid. By substantially free from ionic liquid is meant a solution that includes 0.5% or less by weight of the ionic liquid, such as 0.1% or less by weight, 0.03% or less by weight, 0.01% or less by weight, 0.003% or less by weight, 0.001% or less by weight, 0.0003% or less by weight, or 0.0001% or less by weight.

Compositions

Aspects of the invention further include a composition including: a fluorous salt of an ionic liquid (e.g., as described herein); and a fluorous solvent (e.g., as described herein). The fluorous salt of the ionic liquid may be dissolved in the fluorous solvent. The fluorous salt of ionic liquid may include a fluorinated ion exchanger counterion. In some instances, the fluorous salt is a salt of an ionic liquid cation (e.g., a cation of one of formulae (I) to (VI), as described herein) and a fluorinated ion exchanger counterion (e.g., a counterion of formula (VII), as described herein). In some cases, the fluorinated ion exchanger counterion is bis((perfluorohexyl)sulfonyl)imide. In some instances, the ionic liquid cation is 1-hexyl-3-methyl-imidazolium. In certain embodiments, the fluorous solvent is methoxyperfluorobutane. The fluorous salt of the ionic liquid may have a partition coefficient in the fluorous solvent (e.g., HFE-7100), relative to water of 99.9% or more, such as 99.95% or more, 99.98% or more, 99.99% or more, 99.995% or more, 99.998% or more, or 99.999% or more. In some embodiments, the ion exchanger composition is soluble (e.g., sparingly soluble) in water. In some embodiments, the ion exchanger composition has a partition coefficient in the fluorous solvent (e.g., HFE-7100), relative to water of 99.8% or less, such as 99% or less, 95% or less, 90% or less, 85% or less or 80% or less, but as the metathesis reaction occurs, the fluorinated ion exchanger counterion forms a new fluorous salt with the ionic liquid cation that has an increased partition coefficient in the fluorous solvent (e.g., as described herein).

Kits and Systems

Also provided by this disclosure are kits for practicing the subject method as described above. In some instances, the kit includes an ion exchanger composition (e.g., as described herein) and a fluorous solvent. In certain instances of the kit, the ion exchanger composition includes a fluorinated ion exchanger counterion (e.g., a counterion of formula (VII), as described herein).

A subject kit may contain one or more of: an ionic liquid in an amount sufficient to lyse cells and denature intracellular metabolic enzymes in the biological sample; a protein and/or lipid adsorbing matrix selected from a reverse phase matrix, an ion exchange matrix and a size exclusion matrix; and instructions for extracting metabolites from the cells of the biological sample. In some embodiments of the kit, the ionic liquid is comprised in an aqueous composition including 30% or more of the ionic liquid by weight.

In some embodiments, the kit is a kit for extracting metabolites from a biological sample. The kit may include: an ionic liquid in an amount sufficient to lyse cells and denature intracellular metabolic enzymes in the biological sample (e.g., as described herein); and an ionic exchange composition including a fluorinated ionic exchange counterion (e.g., as described herein). In some embodiments of the kit, the ionic liquid is comprised in an aqueous composition including 30% or more of the ionic liquid by weight. In some embodiments of the method, the ionic liquid includes 1-hexyl-3-methyl-imidazolium. In certain instances, the kit further includes one or more components selected from the group consisting of: a fluorous solvent; a protein and/or lipid adsorbing matrix selected from a reverse phase matrix, an ion exchange matrix and a size exclusion matrix; and instructions for extracting metabolites from the cells of the biological sample.

The kit may also include containers, measurement devices and instruments for performing the subject methods, e.g., vials, agitators, shakers, vortexers, pipets, filter membranes, etc. The various components of the kit may be present in separate containers or certain compatible components may be pre-combined into a single container, as desired. In certain instances of the kit, the ionic exchange composition is disposed in a plurality of containers. In certain instances of the kit, the protein and/or lipid adsorbing matrix is disposed in a plurality of containers. Any convenient containers may be utilized, including single containers such as vials, tubes, or bottles, and multi-well containers, such as multi-well plates, multiplexed tubes, filter tubes, etc. In some cases, the plurality of containers is a multiwell plate.

In addition to above-mentioned components, the subject kits may further include instructions for using the components of the kit to practice the subject methods, i.e., to provide instructions for sample analysis. The instructions for practicing the subject methods are generally recorded on a suitable recording medium. For example, the instructions may be printed on a substrate, such as paper or plastic, etc. As such, the instructions may be present in the kits as a package insert, in the labeling of the container of the kit or components thereof (i.e., associated with the packaging or subpackaging) etc. In other embodiments, the instructions are present as an electronic storage data file present on a suitable computer readable storage medium, e.g., CD-ROM, diskette, etc. In yet other embodiments, the actual instructions are not present in the kit, but means for obtaining the instructions from a remote source, e.g., via the internet, are provided. An example of this embodiment is a kit that includes a web address where the instructions can be viewed and/or from which the instructions can be downloaded. As with the instructions, this means for obtaining the instructions is recorded on a suitable substrate.

Also provided is a system for analytical sample treatment, including a container having disposed therein: an ion exchanger composition; and a fluorous solvent. In some embodiments of the system, the ion exchanger composition includes a fluorinated ion exchanger counterion. In certain instances, the system includes a plurality of the containers, each container having disposed therein the ion exchanger composition and the fluorous solvent. In some cases, the plurality of containers is a multiwell plate. Any convenient containers may be utilized in the subject systems, including single containers such as vials, tubes, or bottles, and multiwell containers, such as multiwell plates (e.g., 96-well plates), multiplexed tubes, filter tubes, etc.

Utility

The method, composition, system and kit described above may be used to analyze analytes of interest in any of a variety of different samples, including metabolites in cellular sample, proteins in proteomics samples, and lipids in biological samples.

Cellular samples of interest include bacterial cells such as *E. coli* cells, and eukaryotic cells such as cells of a lower eukaryote, e.g., yeast, or a higher eukaryote such as a plant (e.g., monocot or dicot) or an animal (e.g., an insect, amphibian, or mammalian etc.). In certain cases, the source of the cells may or may not have a cell wall, and in certain embodiments, the cells may be photosynthetic or non-photosynthetic, oleaginous or non-oleaginous. In particular embodiments, the cells are not algae. The cells may be cultured cells, or, in certain embodiments, cells from a tissue.

The method described above may be used for metabolomics studies, i.e., systematic studies of the unique chemical fingerprints that are associated with specific cellular processes and the study of their metabolite profiles. The metabolome represents the complete set of small-molecule metabolites (such as metabolic intermediates, hormones and other signaling molecules, and secondary metabolites) to be found within a biological sample, such as a single organism.

The subject method, composition, system and kit may be employed in a variety of drug discovery, research and diagnostic applications. For example, a subject method may be employed in a variety of applications that include, but are not limited to, diagnosis or monitoring of a disease or condition (where the presence of metabolic profile is indicative of a disease or condition), discovery of drug targets (where, e.g., of metabolic profile associated with a disease or condition and may be targeted for drug therapy), drug screening (where the effects of a drug are monitored by assessing a metabolic profile), determining drug susceptibility (where drug susceptibility is associated with a particular metabolic profile) and basic research (where is it desirable to identify the a metabolic profile in a sample, or, in certain embodiments, the relative levels of a particular metabolites in two or more samples).

In certain embodiments, relative levels of a set of metabolites in two or more different nucleic acid samples may be obtained using the above methods, and compared. In these embodiments, the results obtained from the above-described methods are usually normalized to the total amount of a control metabolite, and compared. This may be done by comparing ratios, or by any other means. In particular embodiments, the nucleic acid profiles of two or more different samples may be compared to identify metabolites that are associated with a particular disease or condition.

In some examples, the different samples may consist of an "experimental" sample, i.e., a sample of interest, and a "control" sample to which the experimental sample may be compared. In many embodiments, the different samples are pairs of cell types, one cell type being a cell type of interest, e.g., an abnormal cell, and the other a control, e.g., normal, cell. If two fractions of cells are compared, the fractions are usually the same fraction from each of the two cells. In certain embodiments, however, two fractions of the same cell may be compared. Exemplary cell type pairs include, for example, cells that are treated (e.g., with environmental or chemical agents such as peptides, hormones, altered temperature, growth condition, physical stress, cellular transformation, etc.), and a normal cell (e.g., a cell that is otherwise identical to the experimental cell except that it is not immortal, infected, or treated, etc.); cells isolated from a tissue biopsy (e.g., from a tissue having a disease such as colon, breast, prostate, lung, skin cancer, or infected with a pathogen etc.) and normal cells from the same tissue, usually from the same patient; cells grown in tissue culture that are immortal (e.g., cells with a proliferative mutation or an immortalizing transgene), infected with a pathogen or a cell isolated from a mammal with a cancer, a disease, a geriatric mammal, or a mammal exposed to a condition, and a cell from a mammal of the same species, preferably from the same family, that is healthy or young; and differentiated cells and non-differentiated cells from the same mammal (e.g., one cell being the progenitor of the other in a mammal, for example).

EMBODIMENTS

Aspects of the present disclosure include a method for removing an ionic liquid from an aqueous sample. In some embodiments, the method includes: (a) combining an aqueous sample including an ionic liquid with an ion exchanger composition including an ion exchanger counterion to produce a solution including a fluorous salt of the ionic liquid, wherein at least one of the ionic liquid and the ion exchanger counterion is fluorinated; (b) contacting the solution with a fluorous affinity material, thereby removing fluorous salt from the solution and producing an aqueous eluate; and (c) collecting the aqueous eluate. In some embodiments of the method, the fluorous affinity material is an immiscible fluorous solvent that extracts the fluorous salt from the solution to produce the aqueous eluate. In some embodiments of the method, the fluorous affinity material is a fluorous affinity chromatography support that adsorbs the fluorous salt from the solution to produce the eluate.

In some embodiments of the method, the ionic liquid includes a cation selected from the group consisting of:

a) Formula (I):

wherein each of $R^1$ and $R^2$ is independently hydrogen, alkyl, substituted alkyl, aryl, substituted aryl, arylalkyl, substituted arylalkyl, heteroalkyl, substituted heteroalkyl, heteroaryl, substituted heteroaryl, heteroarylalkyl, substituted heteroarylalkyl;

b) Formula (II):

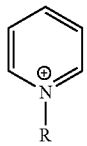

wherein R is hydrogen, alkyl, substituted alkyl, aryl, substituted aryl, arylalkyl, substituted arylalkyl, heteroalkyl, substituted heteroalkyl, heteroaryl, substituted heteroaryl, heteroarylalkyl, substituted heteroarylalkyl;

c) Formula (III):

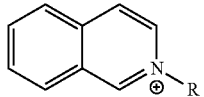

wherein R is hydrogen, alkyl, substituted alkyl, aryl, substituted aryl, arylalkyl, substituted arylalkyl, heteroalkyl, substituted heteroalkyl, heteroaryl, substituted heteroaryl, heteroarylalkyl, substituted heteroarylalkyl;

d) Formula (IV):

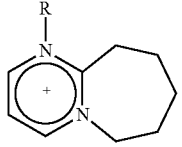

wherein R is hydrogen, alkyl, substituted alkyl, aryl, substituted aryl, arylalkyl, substituted arylalkyl, heteroalkyl, substituted heteroalkyl, heteroaryl, substituted heteroaryl, heteroarylalkyl, substituted heteroarylalkyl;

e) Formula (V):

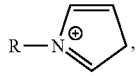

wherein each of R is hydrogen, alkyl, substituted alkyl, aryl, substituted aryl, arylalkyl, substituted arylalkyl, heteroalkyl, substituted heteroalkyl, heteroaryl, substituted heteroaryl, heteroarylalkyl, substituted heteroarylalkyl; and f) Formula (VI):

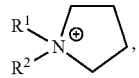

wherein each of $R^1$ and $R^2$ is independently hydrogen, alkyl, substituted alkyl, aryl, substituted aryl, arylalkyl, substituted arylalkyl, heteroalkyl, substituted heteroalkyl, heteroaryl, substituted heteroaryl, heteroarylalkyl, substituted heteroarylalkyl. In some embodiments, the ionic liquid includes 1-hexyl-3-methyl-imidazolium.

In some embodiments of the method, the ion exchanger counterion is a fluorinated counterion described by the formula (VII): $[Z^1-(CH_2)_m-SO_2-N(^-)SO_2-(CH_2)_p-Z^2] \cdot M^+$ (VII) where: $Z^1$ and $Z^2$ are independently a perfluoroalkyl, an alkyl, a substituted alkyl, a perfluoroaryl, an aryl, or a substituted aryl, wherein $Z^1$ and $Z^2$ include together a combined total of 8 or more fluorinated carbon atoms; m and p are independently 0, 1 or 2; and $M^+$ is a cation. In some embodiments of the method, the ion exchanger counterion is bisnonafluoro-1-butanesulfonimidate. In some embodiments of the method, the ion exchanger counterion is bis((perfluorohexyl)sulfonyl)imide. In some embodiments of the method, the ion exchanger composition includes a salt of the ion exchanger counterion selected from silver, lithium, sodium and potassium. In some embodiments of the method, the ion exchanger composition includes a silver salt of the ion exchanger counterion. In some embodiments of the method, step (a) further includes producing an insoluble silver salt.

In some embodiments, the method further includes, prior to step (a), contacting the aqueous sample including an ionic liquid with a reverse phase substrate, thereby adsorbing proteins and/or lipids on the reverse phase substrate, if present in the aqueous sample. In some embodiments, the method further includes analyzing the eluate by mass spectrometry.

In some embodiments, the method further includes: lysing cells of a biological sample; and contacting a biological sample with an amount of the ionic liquid sufficient to denature intracellular metabolic enzymes in the biological sample to produce the aqueous sample.

Also provided is a method for preparation of a cellular sample for analysis. In some embodiments, the method includes: (a) contacting a cell with an amount of an ionic liquid composition sufficient to lyse the cell and produce an aqueous sample including an ionic liquid; (b) contacting the aqueous sample with a reverse phase substrate, thereby adsorbing proteins and/or lipids of the cell on the reverse phase substrate and producing a contacted aqueous sample; (c) combining the contacted aqueous sample either sequentially or simultaneously with: (i) an ion exchanger composition including a fluorinated ion exchanger counterion to produce a fluorous salt of the ionic liquid; and (ii) an immiscible fluorous solvent, thereby extracting the fluorous salt into the fluorous affinity liquid and producing an aqueous eluate; and (d) collecting the aqueous eluate of step (c); and optionally repeating step (c) one or more times on the aqueous eluate until a desired level of fluorous salt in the aqueous eluate is achieved.

In some embodiments, the method further includes contacting the aqueous eluate with a fluorous affinity chromatography support, thereby adsorbing residual fluorous salt from the aqueous eluate. In some embodiments, the method further includes analyzing the aqueous eluate by mass spectrometry. In some embodiments of the method, the ionic liquid composition is an aqueous composition including 30% or more of an ionic liquid. In some embodiments of the method, the ionic liquid includes 1-hexyl-3-methyl-imidazolium. In some embodiments of the method, the ion exchanger composition includes a silver salt of the fluorinated ion exchanger counterion. In some embodiments of the method, the fluorinated ion exchanger counterion is bis((perfluorohexyl)sulfonyl)imide. In some embodiments of the method, the fluorous solvent is methoxyperfluorobutane. In some embodiments of the method, the method further includes eluting the proteins from the reverse phase substrate and analyzing the proteins by mass spectrometry.

Also provided is a composition including a fluorous salt of an ionic liquid and a fluorous solvent. In some embodiments of the composition, the fluorous salt of ionic liquid includes a fluorinated ion exchanger counterion. In some embodiments of the composition, the fluorinated ion exchanger counterion is described by the formula (VII):

[$Z^1$—$(CH_2)_m$—$SO_2$—$N(^-)SO_2$—$(CH_2)_p$—$Z^2$].$M^+$    (VII)

where: $Z^1$ and $Z^2$ are independently a perfluoroalkyl, an alkyl, a substituted alkyl, a perfluoroaryl, an aryl, or a substituted aryl, wherein $Z^1$ and $Z^2$ include together a combined total of 8 or more fluorinated carbon atoms; m and p are independently 0, 1 or 2; and $M^+$ is a cation. In some embodiments of the composition, the fluorinated ion exchanger counterion is bis((perfluorohexyl)sulfonyl)imide. In some embodiments of the composition, the fluorous salt of an ionic liquid includes a cation ($M^+$) selected from the group consisting of:

a) Formula (I):

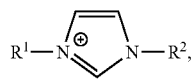

wherein each of $R^1$ and $R^2$ is independently hydrogen, alkyl, substituted alkyl, aryl, substituted aryl, arylalkyl, substituted arylalkyl, heteroalkyl, substituted heteroalkyl, heteroaryl, substituted heteroaryl, heteroarylalkyl, substituted heteroarylalkyl;

b) Formula (II):

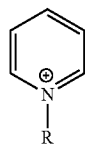

wherein R is hydrogen, alkyl, substituted alkyl, aryl, substituted aryl, arylalkyl, substituted arylalkyl, heteroalkyl, substituted heteroalkyl, heteroaryl, substituted heteroaryl, heteroarylalkyl, substituted heteroarylalkyl;

c) Formula (III):

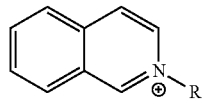

wherein R is hydrogen, alkyl, substituted alkyl, aryl, substituted aryl, arylalkyl, substituted arylalkyl, heteroalkyl, substituted heteroalkyl, heteroaryl, substituted heteroaryl, heteroarylalkyl, substituted heteroarylalkyl;

d) Formula (IV):

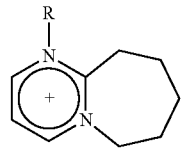

wherein R is hydrogen, alkyl, substituted alkyl, aryl, substituted aryl, arylalkyl, substituted arylalkyl, heteroalkyl, substituted heteroalkyl, heteroaryl, substituted heteroaryl, heteroarylalkyl, substituted heteroarylalkyl;

e) Formula (V):

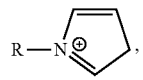

wherein each of $R^1$ and $R^2$ is independently hydrogen, alkyl, substituted alkyl, aryl, substituted aryl, arylalkyl, substituted arylalkyl, heteroalkyl, substituted heteroalkyl, heteroaryl, substituted heteroaryl, heteroarylalkyl, substituted heteroarylalkyl; and f) Formula (VI):

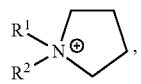

wherein each of $R^1$ and $R^2$ is independently hydrogen, alkyl, substituted alkyl, aryl, substituted aryl, arylalkyl, substituted arylalkyl, heteroalkyl, substituted heteroalkyl, heteroaryl, substituted heteroaryl, heteroarylalkyl, substituted heteroarylalkyl. In some embodiments of the composition, the cation is 1-hexyl-3-methyl-imidazolium. In some embodiments of the composition, the fluorous solvent is methoxyperfluorobutane.

Also provided is a kit for extracting metabolites from a biological sample. In some embodiments, the kit includes an ionic exchange composition including a fluorinated ion exchanger counterion and a fluorous solvent. In some embodiments, the kit further includes one or more components selected from the group consisting of: an ionic liquid in an amount sufficient to lyse cells and denature intracellular metabolic enzymes in the biological sample; a protein and/or lipid adsorbing matrix selected from a reverse phase matrix, an ion exchange matrix and a size exclusion matrix; and instructions for extracting metabolites from the cells of the biological sample. In some embodiments of the kit, the ion exchanger composition is disposed in a plurality of containers. In some embodiments of the kit, the protein and/or lipid adsorbing matrix is disposed in a plurality of containers. In some embodiments of the kit, the plurality of containers is a multiwell plate.

Also provided is a kit that includes an ionic liquid in an amount sufficient to lyse cells and denature intracellular metabolic enzymes in the biological sample; and an ion exchanger composition including a fluorinated ion exchanger counterion. In some embodiments, the kit, further includes one or more components selected from the group consisting of: a fluorous solvent; a protein and/or lipid adsorbing matrix selected from a reverse phase matrix, an ion exchange matrix and a size exclusion matrix; and instructions for extracting metabolites from the cells of the biological sample. In some embodiments of the kit, the ion exchanger composition is disposed in a plurality of containers. In some embodiments of the kit, the protein and/or lipid adsorbing matrix is disposed in a plurality of containers. In some embodiments of the kit, the plurality of containers is a multiwell plate.

Also provided is a system for analytical sample treatment. In some embodiments, the system includes a container having disposed therein: an ionic exchange composition including a fluorinated ion exchanger counterion; and a fluorous solvent. In some embodiments, the system includes a plurality of the containers, each container having disposed therein the ionic exchange composition and the fluorous solvent.

Alternative Embodiments A

Further details of some alternative embodiments of the subject method, and systems and kits for performing the same are described below.

In some embodiments, the method includes: lysing cells of a biological sample; and contacting the biological sample with an amount of ionic liquid sufficient to denature intracellular metabolic enzymes in the biological sample to produce a contacted cellular sample. In certain embodiments of the method, the contacting the biological sample with the ionic liquid lyses the cells of the biological sample. In certain embodiments, the method further includes mixing the contacted cellular sample with an organic solvent to produce an ionic liquid-organic solvent composition. In certain embodiments of the method, mixing the contacted cellular sample with the organic solvent includes producing a dispersed microdroplet ionic liquid-organic solvent composition. In certain embodiments, the method further includes contacting the ionic liquid-organic solvent composition with an ion exchange composition to produce a second ionic liquid-organic solvent composition. In certain embodiments of the method, the ion exchange composition is a second ionic liquid. In certain embodiments of the method, the ion exchange composition includes lithium bis[(trifluoromethane)sulfonyl]imide (LiNTf$_2$). In certain embodiments, the method further includes extracting metabolites from the ionic liquid.

In certain embodiments of the method, the ionic liquid includes a cation selected from the group consisting of:

a) Formula (I):

wherein each of $R^1$ and $R^2$ is independently hydrogen, alkyl, substituted alkyl, aryl, substituted aryl, arylalkyl, substituted arylalkyl, heteroalkyl, substituted heteroalkyl, heteroaryl, substituted heteroaryl, heteroarylalkyl, substituted heteroarylalkyl; or b) Formula (II):

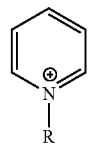

wherein R is hydrogen, alkyl, substituted alkyl, aryl, substituted aryl, arylalkyl, substituted arylalkyl, heteroalkyl, substituted heteroalkyl, heteroaryl, substituted heteroaryl, heteroarylalkyl, substituted heteroarylalkyl; or c) Formula (III):

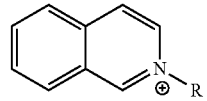

wherein R is hydrogen, alkyl, substituted alkyl, aryl, substituted aryl, arylalkyl, substituted arylalkyl, heteroalkyl, substituted heteroalkyl, heteroaryl, substituted heteroaryl, heteroarylalkyl, substituted heteroarylalkyl; or d) Formula (IV):

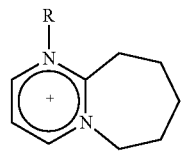

wherein R is hydrogen, alkyl, substituted alkyl, aryl, substituted aryl, arylalkyl, substituted arylalkyl, heteroalkyl, substituted heteroalkyl, heteroaryl, substituted heteroaryl, heteroarylalkyl, substituted heteroarylalkyl; or e) Formula (V):

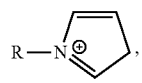

wherein each of $R^1$ and $R^2$ is independently hydrogen, alkyl, substituted alkyl, aryl, substituted aryl, arylalkyl, substituted arylalkyl, heteroalkyl, substituted heteroalkyl, heteroaryl, substituted heteroaryl, heteroarylalkyl, substituted heteroarylalkyl; or f) Formula (VI):

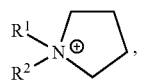

wherein each of $R^1$ and $R^2$ is independently hydrogen, alkyl, substituted alkyl, aryl, substituted aryl, arylalkyl, substituted arylalkyl, heteroalkyl, substituted heteroalkyl, heteroaryl, substituted heteroaryl, heteroarylalkyl, substituted heteroarylalkyl.

In certain embodiments of the method, the ionic liquid includes 1-butyl-3-methyl-imidazol-3-ium. In certain embodiments of the method, the biological sample is contacted with the ionic liquid at room temperature. In certain embodiments, the method further includes filtering the biological sample to remove culture media and extracellular components from the cells prior to contacting with the ionic liquid.

Also provided is a system for high throughput analysis of cellular metabolites. In some embodiments, the system includes: a contacting apparatus configured for contacting one or more biological samples with an ionic liquid; a sampling device configured to provide one or more biological samples including cells to the contacting apparatus; and an ionic liquid solvent chamber configured to provide one or more ionic liquids to the contacting apparatus. In certain embodiments, the system further includes an ion exchange composition chamber configured to provide one or more ion exchange compositions to the contacting apparatus. In certain embodiments of the system, the ion exchange composition includes lithium bis[(trifluoromethane)sulfonyl]imide (LiNTf$_2$). In certain embodiments, the system further includes a sample analyzer. In certain embodiments of the system, the sample analyzer includes liquid-chromatography-mass spectrometry or gas chromatography-mass spectrometry. In certain embodiments of the system, the ionic liquid includes a cation selected from the group consisting of: a) Formula (I):

wherein each of $R^1$ and $R^2$ is independently hydrogen, alkyl, substituted alkyl, aryl, substituted aryl, arylalkyl, substituted arylalkyl, heteroalkyl, substituted heteroalkyl, heteroaryl, substituted heteroaryl, heteroarylalkyl, substituted heteroarylalkyl; or b) Formula (II):

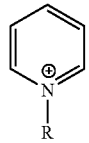

wherein R is hydrogen, alkyl, substituted alkyl, aryl, substituted aryl, arylalkyl, substituted arylalkyl, heteroalkyl, substituted heteroalkyl, heteroaryl, substituted heteroaryl, heteroarylalkyl, substituted heteroarylalkyl; or c) Formula (III):

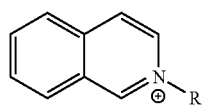

wherein R is hydrogen, alkyl, substituted alkyl, aryl, substituted aryl, arylalkyl, substituted arylalkyl, heteroalkyl, substituted heteroalkyl, heteroaryl, substituted heteroaryl, heteroarylalkyl, substituted heteroarylalkyl; or d) Formula (IV):

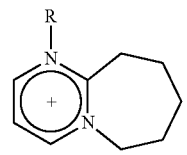

wherein R is hydrogen, alkyl, substituted alkyl, aryl, substituted aryl, arylalkyl, substituted arylalkyl, heteroalkyl, substituted heteroalkyl, heteroaryl, substituted heteroaryl, heteroarylalkyl, substituted heteroarylalkyl; or e) Formula (V):

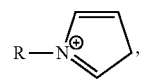

wherein each of $R^1$ and $R^2$ is independently hydrogen, alkyl, substituted alkyl, aryl, substituted aryl, arylalkyl, substituted arylalkyl, heteroalkyl, substituted heteroalkyl, heteroaryl, substituted heteroaryl, heteroarylalkyl, substituted heteroarylalkyl; or f) Formula (VI):

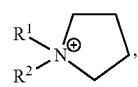

wherein each of $R^1$ and $R^2$ is independently hydrogen, alkyl, substituted alkyl, aryl, substituted aryl, arylalkyl, substituted arylalkyl, heteroalkyl, substituted heteroalkyl, heteroaryl, substituted heteroaryl, heteroarylalkyl, substituted heteroarylalkyl.

In certain embodiments, the system further includes a processor including memory operably coupled to the processor, wherein the memory includes instructions stored thereon, the instructions including: algorithm for contacting one or more biological samples with an amount of ionic liquid sufficient to lyse cells and denature intracellular metabolic enzymes in the biological sample; algorithm for mixing the ionic liquid with an organic solvent to produce a first ionic liquid-organic solvent two-phase composition; algorithm for employing an agitator to agitate the first ionic liquid-organic solvent two-phase composition to produce a dispersed microdroplet composition; algorithm for contacting dispersed microdroplet composition with an ion exchange composition to produce a second ionic liquid-organic solvent two-phase composition; algorithm for separating the ionic liquid from the organic solvent and extracting metabolites from the ionic liquid; and instructions for identifying one or more metabolites extracted from the ionic liquid.

Also provided is a kit for extracting metabolites from a biological sample. In some embodiments, the kit includes: one or more ionic liquids in an amount sufficient to lyse cells and denature intracellular metabolic enzymes in the biological sample; one or more organic solvents; one or more ion exchange compositions; and instructions for extracting metabolites from the cells of the biological sample.

Further details of some implementation of the methods, and some components of the systems and kits of the alternative embodiments described above may be described in specification and figures of U.S. application Ser. No. 14/205, 100, filed Mar. 11, 2014, which application is incorporated herein by reference.

Alternative Embodiments B

Further alternative embodiments of the subject method are described below.

In some embodiments, the method is a method for removing an ionic liquid from an aqueous sample. In some embodiments, the method comprises: (a) combining an aqueous sample comprising an ionic liquid with a perfluorous counterion to produce an aqueous solution comprising a perfluorous salt of the ionic liquid; (b) contacting the aqueous solution with a fluorous affinity substrate, thereby absorbing the perfluorous salt on the fluorous affinity substrate; and (c) collecting the eluate of step (b). In certain embodiments, the method further comprises, prior to step (b), extracting a portion of the perfluorous salt of the ionic liquid from the aqueous sample using a perfluorous ion exchanger solution that is immiscible with the aqueous sample, wherein the perfluorous ion exchanger solution comprises the perfluorous counterion. In certain embodiments of the method, the aqueous sample comprises cellular metabolites. In certain embodiments, the method further comprises analyzing the eluate using mass spectroscopy.

In certain embodiments of the method, the perfluorous counterion is described by formula (VII): $Z^1$-$L^1$-A-(-$L^2$-$Z^2$)$_n$ (VII) wherein: $Z^1$ is a perfluoroalkyl, a perfluoroaryl, a fluorinated alkyl or a fluorinated aryl; n is 0, 1, 2 or 3; each $Z^2$, if present, is independently selected from the group consisting of a perfluoroalkyl, a perfluoroaryl, an alkyl, a substituted alkyl, an aryl and a substituted aryl; A is a charged moiety capable of acting as a counterion to the ionic liquid; and $L^1$ and $L^2$ are independently a covalent bond or a linker. In certain embodiments of the method, the perfluorous counterion is described by formula (VIII): $Z^1$-$L^1$-A (VIII) wherein $Z^1$, $L^1$ and A are as defined above. In certain embodiments of the method, A is an organic anion selected from a sulfonimidate, a sulfonate, a carboxylate, a phosphate and a borate. In certain embodiments of the method, when n=1, A is —$SO_2N(^-)SO_2$—. In certain embodiments of the method, when n=0, A is —$SO_2NH(^-)$. In certain embodiments of the method, $L^1$ and each $L^2$ are independently a $C_1$-$C_6$ alkyl linker or a covalent bond. In certain embodiments of the method, $L^1$ and each $L^2$ are independently selected from —$CH_2CH_2$— or a covalent bond. In certain embodiments of the method, $Z^1$ and $Z^2$ are each independently a perfluoroalkyl group (e.g., comprising 4 or more fluorinated carbon atoms). In certain embodiments of the method, $Z^1$ and each $Z^2$ comprise together a combined total of 8 or more fluorinated carbon atoms (e.g., 10 or more, 12 or more, 14 or more, 16 or more, 18 or more or even 20 or more fluorinated carbon atoms). In certain embodiments of the method, the perfluorous counterion is described by the formula (IX): [$Z^1$—($CH_2$)$_m$—$SO_2$—N($^-$)$SO_2$—($CH_2$)$_p$—$Z^2$].$M^+$ (IX), wherein: $Z^1$ and $Z^2$ are independently a perfluoroalkyl, an alkyl, a substituted alkyl, a perfluoroaryl, an aryl, or a substituted aryl, wherein $Z^1$ and $Z^2$ comprise together a combined total of 8 or more fluorinated carbon atoms (e.g., 10 or more, 12 or more, 14 or more, 16 or more, 18 or more or even 20 or more fluorinated carbon atoms); m and p are independently 0, 1 or 2; and $M^+$ is a cation (e.g., $Li^+$, $K^+$, etc). In certain embodiments of the method, the perfluorous counterion is a bisnonafluoro-1-butanesulfonimidate.

In some embodiments, the method comprises: (a) extracting an aqueous sample comprising an ionic liquid with a perfluorous ion exchanger phase comprising a perfluorous counterion to produce an extracted aqueous sample, wherein the perfluorous counterion and the ionic liquid form a perfluorous salt that is soluble in the perfluorous ion exchanger phase; (b) passing the extracted aqueous solution through a fluorous affinity chromatography column under conditions in which the perfluorous salt, if present, is absorbed to the column; and (c) collecting the eluate of the extracted aqueous solution. In certain embodiments of the method, the aqueous sample comprises cellular metabolites and the method further comprises analyzing the aqueous solution using mass spectroscopy.

In some embodiments, the method comprises: (a) combining an aqueous sample comprising an ionic liquid with an ion exchanger counterion to produce an aqueous solution comprising a perfluorous salt of the ionic liquid, wherein at least one of the ionic liquid and the ion exchanger counterion is fluorinated; (b) contacting the aqueous solution with a fluorous affinity substrate, thereby absorbing the perfluorous salt on the fluorous affinity substrate; and (c) collecting the eluate of step (b). In certain embodiments of the method, the ionic liquid is fluorinated. In certain embodiments of the method, the ion exchanger counterion is a perfluorous counterion. In certain embodiments of the method, the aqueous sample comprises cellular metabolites and the method further comprises analyzing the eluate using mass spectroscopy.

Figure 10:
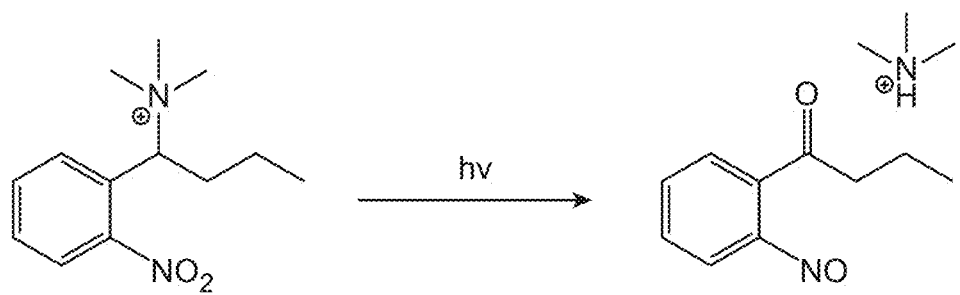
FIG. 10 illustrates a photocleavable ionic liquid for use in methods according to an alternative embodiment of the subject methods.

In some embodiments, the method may involve a photocleavable ionic liquid. In such cases, removal of the photocleavable ionic liquid from a sample of interest may be facilitated by application of light to photocleave the ionic liquid, see e.g., FIG. 10. Cleavage of the ionic liquid may provide two or more fragments, where some of the fragments produced are more easily extracted or separated from the sample of interest using the subject methods. In some cases, photocleavage of the ionic liquid produces fragments that provide for an improved analysis by mass spectroscopy because the fragments are either: more easily removed from the analytical sample; or cause less interference during MS analysis and thus have less need to be removed prior to analysis.

Figure 11:
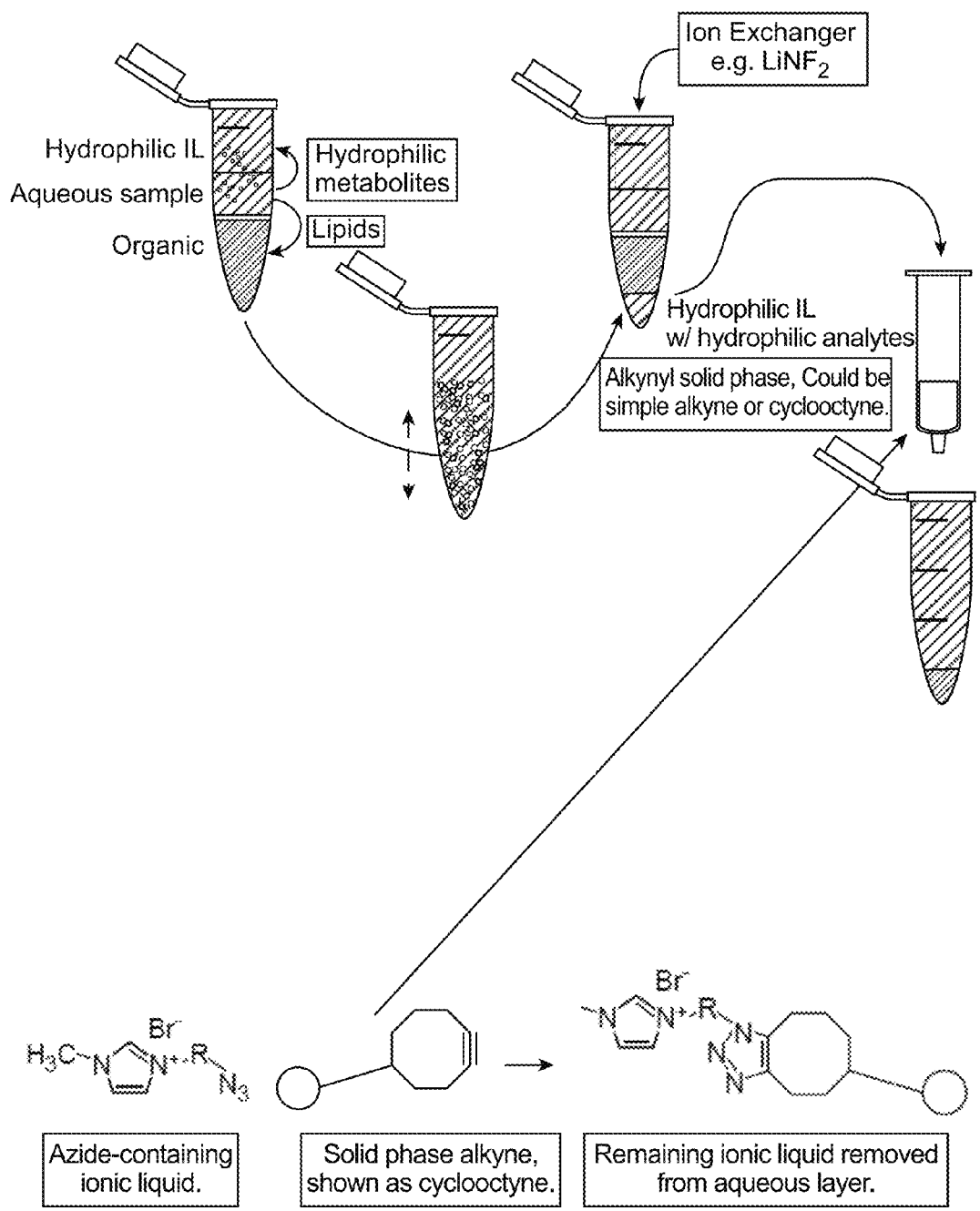
FIG. 11 schematically illustrates a workflow for methods according a further alternative embodiment of the subject method. IL Requirements: 1. Efficient extraction of hydrophilic metabolites from water; 2. Less dense than water; 3. After metathesis reaction, more dense than water or organic; 4. Disperses in water and organic; 5. Nonelutropic properties by chromatographic cleanup. Note: target metabolites include hydrophilic, polar and medium polarity.
Figure 12:
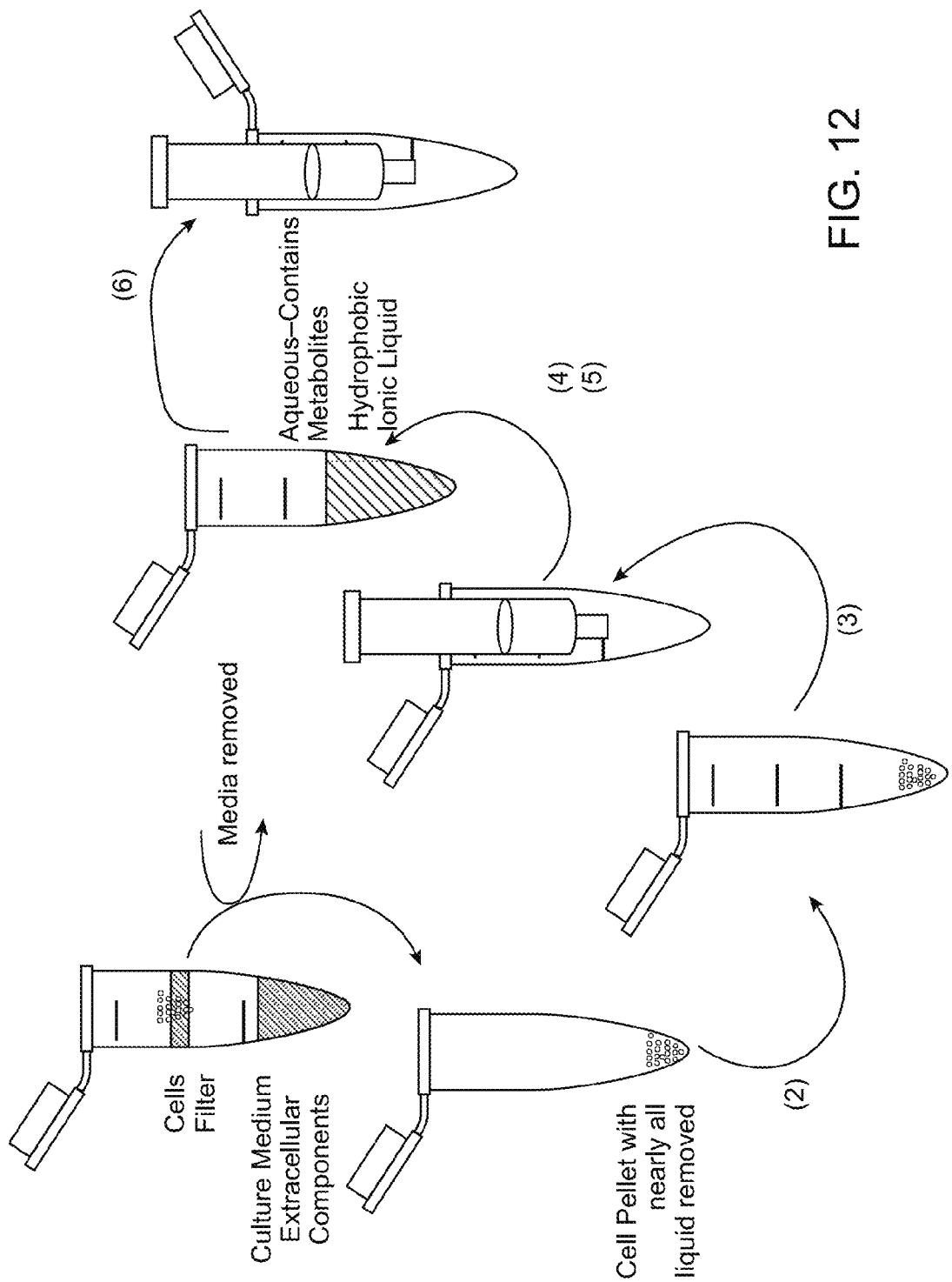
FIG. 12 schematically illustrates an ionic liquid metabolomics sample preparation workflow for methods according one embodiment of the subject method, using an ionic liquid containing an excess of the water immiscible anion of the ionic liquid (as a metal salt) (potassium Bisnonafluoro-1- butanesulfonimidate (KF-4C-NTf2)) to extract the ionic liquid cation out of the aqueous solution: (2) Add Ionic Liquid/Water solution-Lyse Cells and quench metabolism. (3) Entire cellular debris with Ionic Liquid/water put Through C18 column to remove proteins. (4) Add Ion Exchanger Solution IL4-F4C-NTt2+KF4C-NTt2. (5) Spin-4000×g; (6) Remove upper aqueous layer, put onto fluorous affinity column.

In some embodiments, the method may involve use of a bioorthogonal conjugation chemistry to remove the ionic liquid from a sample of interest via the formation of a covalent bond to a support including a compatible functional group. In some embodiments, the ionic liquid includes a first functional group capable of conjugation to a second compatible functional group. Any convenient conjugation chemistries may be utilized. FIG. 11 illustrates one embodiment, where an azide-linked ionic liquid that may be conjugated to an alkyne-solid support (e.g., cyclooctyne-solid support) via Click chemistry to produce an immobilized ionic liquid which may be subsequently removed from a sample of interest. In other embodiments, an alkyne-linked ionic liquid is conjugated to an azide-solid support via Click chemistry to produce an immobilized ionic liquid which may be subsequently removed from a sample of interest.

Also provided are systems and kits for practicing the embodiments of the method.

Further details of some implementation of the alternative embodiments of the method and components of systems and kits for practicing the same are described above may be described in specifications and figures of U.S. provisional application Ser. No. 62/016,003, filed on Jun. 23, 2014; and U.S. provisional application Ser. No. 62/051,804, filed on Sep. 17, 2014, which applications are incorporated herein by reference.

Alternative Embodiments C

Further alternative embodiments of the subject method are described below.

In some embodiments, the method is a method for processing a sample including: (a) combining an aqueous sample including an ionic liquid with a magnetic ionic exchanger to produce an aqueous solution including a magnetic salt of the ionic liquid; (b) applying an external magnetic field to the product of step (a) to remove the magnetic salt from the sample; and (c) collecting the sample. In certain embodiments of the method, the combining step (a) results in a biphasic liquid. In certain embodiments of the method, the aqueous sample includes cellular metabolites. In certain embodiments, the method further includes analyzing the eluate using mass spectroscopy. In certain embodiments of the method, the magnetic ionic exchanger includes a transition metal. In certain embodiments of the method, the ionic salt is transition metal complex susceptible to an external magnetic field. In certain embodiments of the method, the magnetic ionic exchanger includes a magnetic counterion capable of forming a salt with the ionic liquid, e.g., imidazolium, that has limited or no solubility in water. In certain embodiments of the method, the magnetic ionic exchanger includes a paramagnetic or ferromagnetic element. In certain embodiments of the method, the magnetic ionic exchanger includes a $CoCl_4$ or $FeCl_4$ counterion.

Further details of some implementation of the alternative embodiments of the method described above may be described in specification and figures of U.S. provisional application Ser. No. 62/049,285, filed on Sep. 11, 2014, which application is incorporated herein by reference.

Alternative Embodiments D

Further alternative embodiments of the subject method are described below.

Figure 9:
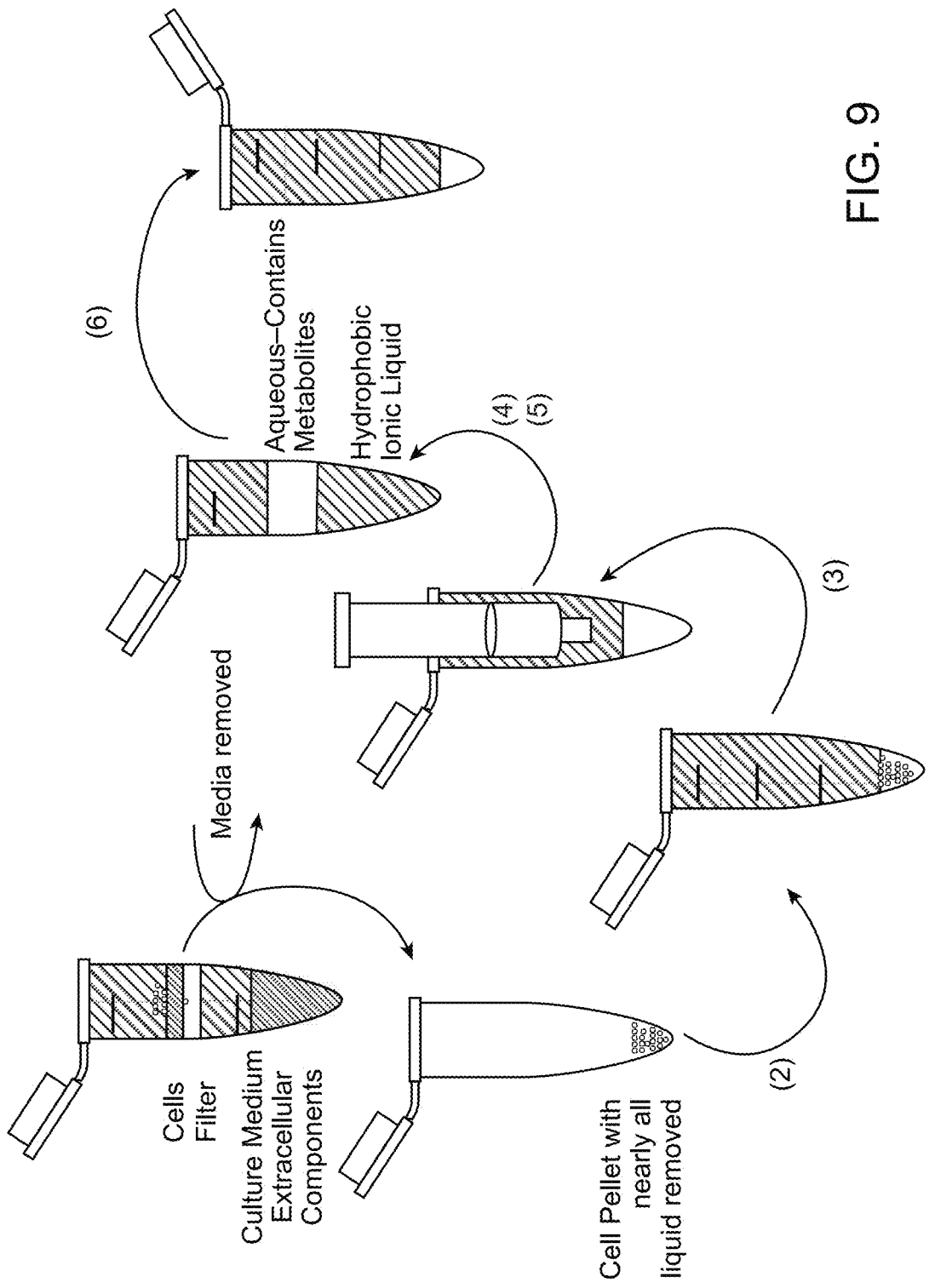
FIG. 9 schematically illustrates a sample preparation workflow for methods according one embodiment of the subject method: (2) Add Ionic Liquid/Water solution-Lyse Cells and quench metabolism; (3) Entire cellular debris with Ionic Liquid/water put through C18 column to remove proteins; (4) Add Aqueous Ion Exchanger Solution e.g. $LiNTf_2$; (5) Spin~4000×g; (6) Remove upper aqueous layer and inject in LC-MS.

In certain cases, the method may involve: a) mixing a cell with an ionic liquid (e.g., an ionic liquid/water solution), thereby quenching metabolism and lysing the cells, and b) performing reverse phase chromatography on the product of step a) (e.g., using a C18 column), thereby removing the protein from the product of step a). These steps do not utilize an organic solvent. In some embodiments, this method may further include: c) adding an aqueous exchange solution ($LiNTf_2$) to the flow through of step b), thereby producing a first aqueous phase that contains metabolites and a second hydrophobic phase containing the ionic liquid. In some embodiments, this method may further include: d) analyzing the metabololites in the aqueous phase, e.g., by LC-MS. An example of the workflow is shown in FIG. 9.

Further details of some implementation of the alternative embodiments of the method described above may be described in the specification and figures of U.S. provisional application Ser. No. 62/016,000, filed on Jun. 23, 2014, which application is incorporated herein by reference.

EXAMPLES

The following example is offered for illustrative purposes only, and is not intended to limit the scope of the present invention in any way.

Example 1

One embodiment of the method utilizes a fluorous oil (HFE-7100, methoxyperfluorobutane) and a silver salt of bis((perfluorohexyl)sulfonyl)imide, which is very water insoluble, along with multiple extractions as a way to remove hexylmethylimidazolium chloride from an aqueous metabolite solution. The HFE-7100 solubilizes the silver(I) bis((perfluorohexyl)sulfonyl)imide just enough so that as the ion exchange reaction starts to occur, the new ionic liquid that is formed helps solubilize the remaining silver(I) bis ((perfluorohexyl)sulfonyl)imide. As a byproduct, the AgCl that is formed is very insoluble in aqueous solutions and precipitates as a new solid. This is important to keep it out of the mass spectrometer for analysis purposes and for cleanliness of the mass spectrometer.

Figure 2:
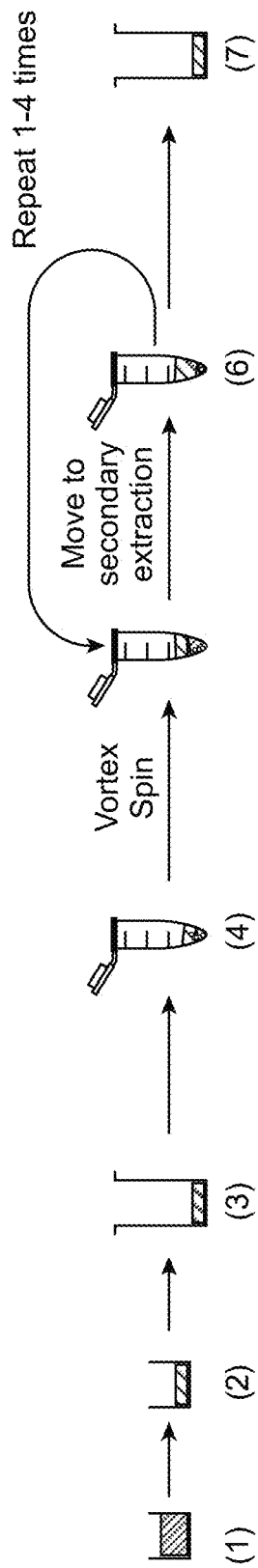
FIG. 2 schematically illustrates an ionic liquid metabolomics sample preparation workflow for methods according one embodiment of the subject method: (1) Fast filter; (2) Lyse/Quench 50 µL 1:1 HMIMCl:$H_2O$; (3) C18 column (remove protein and lipids); (4) Extract HMIMCl 225 µL $H_2O$, 100 µL HFE-7100, 1.1 equivalents $Ag^{+-}$-N(perfluorohexylsulfonyl)$_2$, (6) 50 µL $H_2O$, 50 µL HFE-7100, 0.05 equivalents $Ag^{+-}$N(perfluorohexylsulfonyl)$_2$; (7) C8-Fluorous SPE (maybe not needed).
Figure 3:
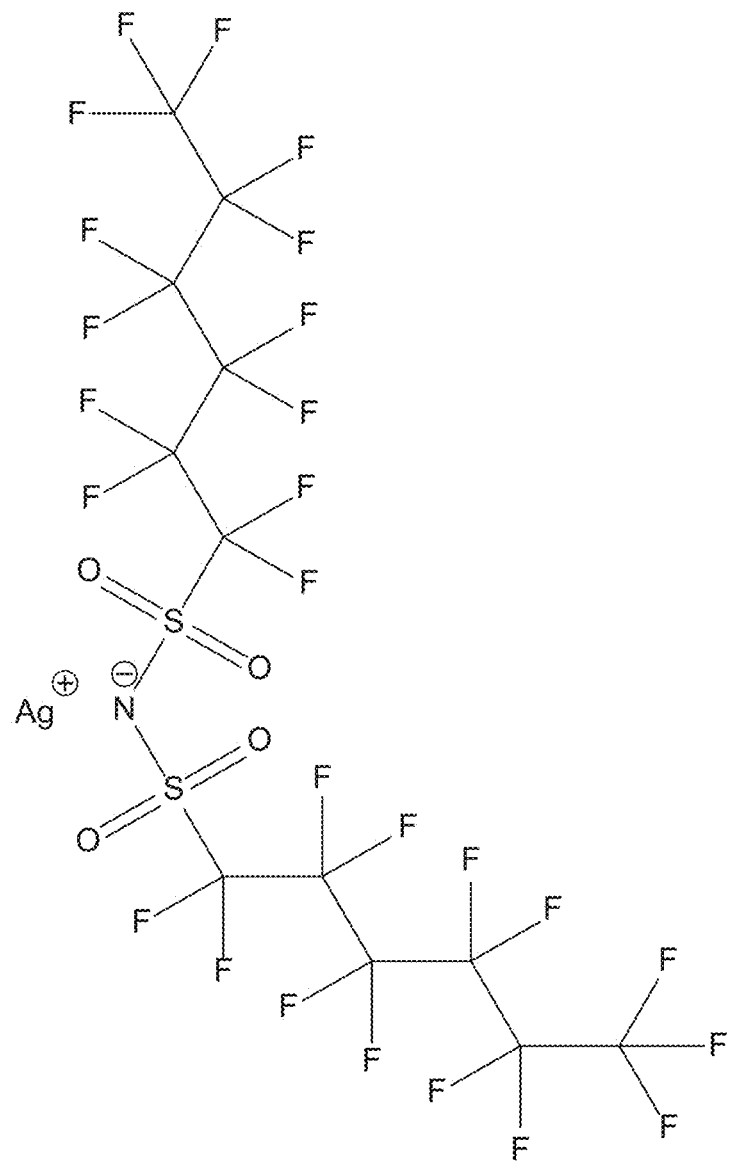
FIG. 3 shows the structure of a silver salt of an ion exchanger of interest (Ag+−NTfn=silver(I) bis((perfluorohexyl)sulfonyl)imide).

One workflow of interest is depicted in FIGS. 1 and 2. In summary the cells are lysed and metabolism is quenched by adding greater than 30% aqueous hexamethylimidazolium chloride (typically 50%) and vortexing, followed by passage through a C18 spin column to remove proteins, which keeps metabolism quenched. Next, the solution is added to a vial containing a fluorous ion exchanger (silver(I) bis((perfluorohexyl)sulfonyl)imide) that is present as the silver (I) salt as a solid in a fluorous solvent (specifically HFE-7100, which is methoxyperfluorobutane). The mixture is vortexed, spun in a centrifuge, and the aqueous layer is transferred to a new vial containing a small amount of the silver(I) bis((perfluorohexyl)sulfonyl)imide in HFE-7100 to do another extraction. This process may be repeated four times and the
aqueous layer is then ready for injection into the MS (mass spectrometer). Optionally, fluorous solid phase extraction can be performed if necessary to remove all traces of the silver(I) bis((perfluorohexyl)sulfonyl)imide.

Figure 4:
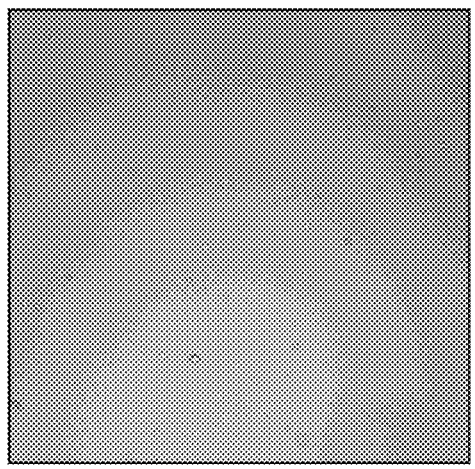
FIG. 4 depicts microscope images demonstrating lysis of yeast cells that have been treated with water (left) or 1:1 water/HMIM-Cl (right) and stained with trypan blue. Left: Yeast cells, 100 µL water, add 2 µL to 18 µL Trypan Blue, 20× magnification. Right: Yeast cells, 50 µL water, 50 µL HMIM-Cl, add 2 µL to 18 µL Trypan Blue, 20× magnification.
Figure 4:
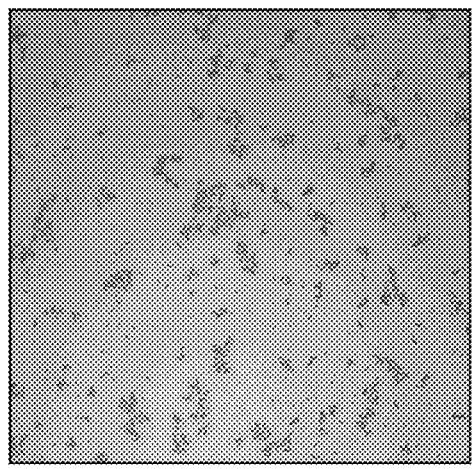

FIG. 4 depicts microscope images demonstrating lysis of yeast cells that have been treated with water (left) or 1:1 water/HMIM-Cl (right) and stained with trypan blue.

Figure 5:
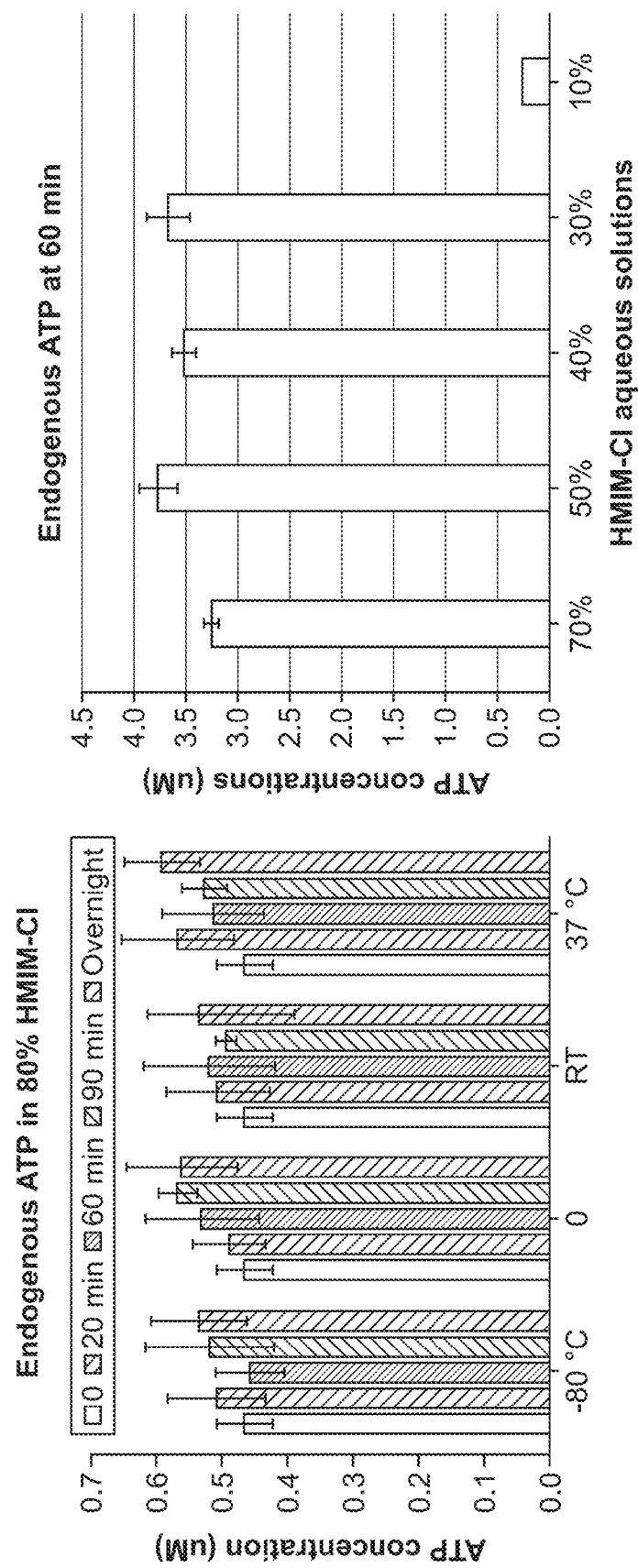
FIG. 5 illustrates the results of an ATP Luciferase assay that demonstrates ATP metabolism in *E. coli* cells remains quenched in aqueous HMIM-Cl solutions.

FIG. 5 illustrates the results of a ATP Luciferase assay that demonstrates ATP metabolism in E. coli cells remains quenched in aqueous HMIM-Cl solutions.

Figure 6:
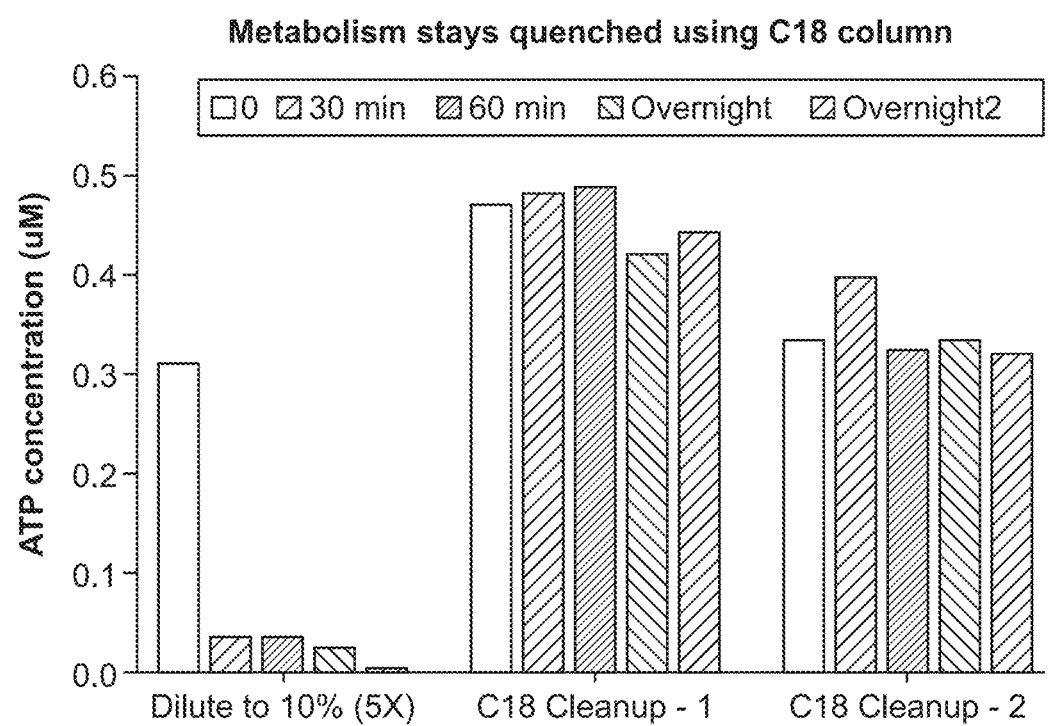
FIG. 6 illustrates the removal of proteins using a C18 SPE (solid phase extraction) prior to ion exchange reaction keeps metabolism quenched.

FIG. 6 illustrates the removal of proteins using a C18 SPE (solid phase extraction) prior to ion exchange reaction keeps metabolism quenched.

FIG. 7 shows extracted ion chromatograms (EIC) for HMIM after each extraction of the aqueous layer using fresh HFE-7100 (methoxyperfluorobutane) and bis((perfluorohexyl)sulfonyl)imide. (A) EIC for HMIM in a blank run, after the initial ion exchange reaction, and two subsequent extractions. (B) The same EICs as in (A), with the initial ion exchange reaction EIC removed to demonstrate the levels go almost back to background.

Example 2

Sample processing and preparation for metabolomic analysis which incorporates into its steps one or more of the following:
1. Quenching—Stopping any metabolic processes such that an accurate snapshot of the current metabolic state of the cells under study can be evaluated.
2. Cell Lysis—The intracellular metabolome is measured. The cell is lysed and the cell contents separated from the extracellular medium.
3. Metabolite Extraction: Metabolic components are extracted from all other cellular components (proteins, nucleic acids, lipids).

4. Metabolite Concentration: Depending on the sensitivity of the analytical technique and the requirements of the experiment, the extracted metabolites are concentrated prior to analysis.

Brief Description of Exemplary Techniques (a) Dispersive Liquid Liquid Microextraction (DLLME), is a sample preparation technique based on formation of a turbid solution by quickly injecting a mixture of an extraction solvent and a disperser solvent into an aqueous solution. The extraction solvent is hydrophobic and of higher density than water while the disperser is miscible with both aqueous and organic phases. The obtained turbid solution results in the large contact area between the fine extraction solvent droplets and aqueous analyte solution, remarkably decreasing the extraction time and increasing the extraction efficiency. DLLME has been widely applied to arrange of analytical samples, primarily environmental.

(b) Ionic Liquids combined with DLLME for preparing a sample where the compounds of interest are extracted into the ionic liquid.

A method for metabolic sample preparation based on Dispersive Liquid Liquid Microextraction (DLLME) utilizing Ionic Liquids (IL) in which the novel ionic liquids rapidly and effectively denature metabolic enzymes to quench metabolism and simultaneously extracting hydrophilic metabolites in the background of cellular components. Ionic Liquids are used in combination with DLLME to simultaneously lyse cells and denature metabolic enzymes in such a way as to rapidly quench metabolism. The workflow may have at least the following benefits:

1. Rapid Cell Lysis and Metabolic Quenching without the use of cryo-conditions.
2. Rapid separation of extra- and intra-cellular components
3. Rapid and Efficient fractionation of intracellular components into hydrophilic and hydrophobic fractions.
4. Robust technique applied to a range of cellular systems without the need of optimization for each cell type
5. Easily adapted to automated, robotic platforms and multiwell plate sample formats.

Example 3

An example workflow includes:
Step 1: Cell Suspension is transferred to a filter tube and rapidly filtered to separate culture media and extra-cellular components from the cell mass.
Step 2: The filtered cells are resuspended in a hydrophilic Ionic Liquid. This simultaneously and rapidly lyses the cells and denatures the metabolic enzymes and consequently quenches metabolic processes.
Step 3: The Ionic Liquid containing the sample is mixed with a hydrophobic organic liquid.
Step 4: The two phase system is agitated forming a dispersed system of ionic liquid microdroplets with a high surface area (without the addition of a dispersant). Hydrophobic components (such as lipids) are extracted into the organic phase. Proteins precipitate. The hydrophilic metabolite analytes are extracted into the ionic liquid.
Step 5: An Ion Exchanger Composition (e.g., LiNTf$_2$) is added causing the Ionic Liquid microdroplets to condense in a salt metathesis reaction and separate from the organic layer.

Step. 6: The Ionic liquid is removed from the metabolite analytes by solid phase microextraction under conditions where the ionic liquid itself does not act as an elutropic solvent during the loading of analytes onto stationary phase.

In the above example, ionic liquids of interest have the following characteristics:
Denature Proteins/Quench Metabolites
Lyse Cells (Yeast)
Extract/Solublize Metabolites of interest
Precipitate/Remove Proteins
Immiscible w/Organic for 2 phase extraction DLLME
Metabolites can be separated by liquid chromatography (e.g., HPLC)

In one example, the ionic liquid include:

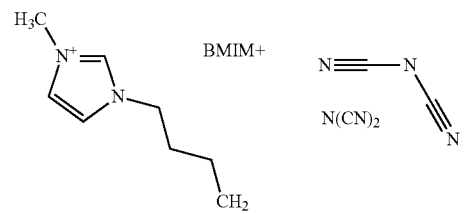

Alternatively, room temperature ionic liquids may include a scaffold structure such as a 1,3 substituted imidazolium cation, a salt can be structured, by varying the R groups and the counter ion to optimize a range of physicochemical properties.

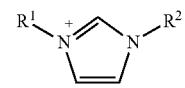

1,3 substituted imidazol-3-ium

For example, in the structure show above, $R^1$ and $R^2$ are selected and adapted based on general physico-chemical properties such as density, solubility, vapor pressure, as desired. In addition, specific substitutions can be made on the R-groups to enhance specific chemical interactions with target groups.

Example 4

An example workflow similar to the steps described above in Example 2 include a three phase system in which an ionic liquid is used that can interact with metabolites to extract them from aqueous solution intermediate between the organic solution.
Step 1: Cell Suspension is transferred to a filter tube and rapidly filtered to separate culture media and extra-cellular components from the cell mass.
Step 2: The filtered cells are resuspended as an aqueous solution in a hydrophilic Ionic Liquid. This would simultaneously rapidly lyse the cells and denature the metabolic enzymes and consequently quench metabolic processes.
Step 3: The Ionic Liquid containing the sample is mixed with a hydrophobic organic liquid.
Step 4: The three phase system is agitated forming a dispersed system of ionic liquid microdroplets with a high surface area (without the addition of a dispersant). Hydrophobic components (such as lipids) are extracted into the organic phase. Proteins precipitate. The hydrophilic metabolite analytes are extracted into the ionic liquid.

Step 5: An Ion Exchanger (e.g., LiNTf$_2$) is added causing the Ionic Liquid microdroplets to condense in metathesis reaction and separate from the organic and aqueous layers.

Step. 6: The Ionic liquid is removed from the metabolite analytes by solid phase microextraction under conditions where the ionic liquid itself does not act as an elutropic solvent during the loading of analytes onto stationary phase.

Example 5

An example workflow similar to the steps described above in Example 2, includes a three phase system in which an ionic liquid is used that can interact with metabolites to extract them from aqueous solution intermediate between the organic solution with the addition of a chaotrope and dispersant to enhance microdroplet formation.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

Accordingly, the preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the embodiments shown and described herein. Rather, the scope and spirit of present invention is embodied by the appended claims.

What is claimed is:

1. A method for removing an ionic liquid from an aqueous sample comprising a cell lysate, the method comprising:
   (a) combining an aqueous sample comprising a cell lysate and an ionic liquid with an ion exchanger composition comprising an ion exchanger counterion, thereby producing a solution comprising the cell lysate and a fluorous salt of the ionic liquid, wherein at least one of the ionic liquid and the ion exchanger counterion is fluorinated;
   (b) contacting the solution with a fluorous affinity material, thereby removing the fluorous salt of the ionic liquid from the solution and producing an aqueous eluate comprising the cell lysate; and
   (c) collecting the aqueous eluate comprising the cell lysate.

2. The method of claim 1, wherein the fluorous affinity material is a fluorous solvent that extracts the fluorous salt from the solution to produce the aqueous eluate, wherein the fluorous solvent is immiscible with the solution.

3. The method of claim 1, wherein the fluorous affinity material is a fluorous affinity chromatography support that adsorbs the fluorous salt from the solution to produce the aqueous eluate.

4. The method of claim 1, wherein the ionic liquid comprises a cation selected from the group consisting of:

a) Formula (I):

wherein each of $R^1$ and $R^2$ is independently hydrogen, alkyl, substituted alkyl, aryl, substituted aryl, arylalkyl, substituted arylalkyl, heteroalkyl, substituted heteroalkyl, heteroaryl, substituted heteroaryl, heteroaryl alkyl, substituted heteroarylalkyl;

b) Formula (II):

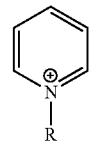

wherein R is hydrogen, alkyl, substituted alkyl, aryl, substituted aryl, arylalkyl, substituted arylalkyl, heteroalkyl, substituted heteroalkyl, heteroaryl, substituted heteroaryl, heteroarylalkyl, substituted heteroarylalkyl;

c) Formula (III):

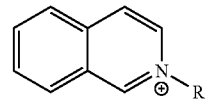

wherein R is hydrogen, alkyl, substituted alkyl, aryl, substituted aryl, arylalkyl, substituted arylalkyl, heteroalkyl, substituted heteroalkyl, heteroaryl, substituted heteroaryl, heteroarylalkyl, substituted heteroarylalkyl;

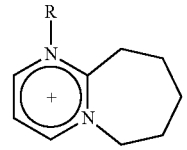

d) Formula (IV):

wherein R is hydrogen, alkyl, substituted alkyl, aryl, substituted aryl, arylalkyl, substituted arylalkyl, heteroalkyl, substituted heteroalkyl, heteroaryl, substituted heteroaryl, heteroarylalkyl, substituted heteroarylalkyl;

e) Formula (V):

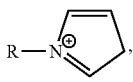

wherein each of R is hydrogen, alkyl, substituted alkyl, aryl, substituted aryl, arylalkyl, substituted arylalkyl, heteroalkyl, substituted heteroalkyl, heteroaryl, substituted heteroaryl, heteroarylalkyl, substituted heteroarylalkyl; and f) Formula (VI):

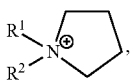

wherein each of $R^1$ and $R^2$ is independently hydrogen, alkyl, substituted alkyl, aryl, substituted aryl, arylalkyl, substituted arylalkyl, heteroalkyl, substituted heteroalkyl, heteroaryl, substituted heteroaryl, heteroaryl alkyl, substituted heteroarylalkyl.

5. The method of claim 1, wherein the ion exchanger counterion is a fluorinated counterion described by the formula (VII):

$$[Z^1\text{—}(CH_2)_m\text{—}SO_2\text{—}N(^-)\text{—}SO_2\text{—}(CH_2)_p\text{—}Z^2]\cdot M^+ \quad \text{(VII)}$$

wherein:
  $Z^1$ and $Z^2$ are independently a perfluoroalkyl, an alkyl, a substituted alkyl, a perfluoroaryl, an aryl, or a substituted aryl, wherein $Z^1$ and $Z^2$ comprise together a combined total of 8 or more fluorinated carbon atoms;
  m and p are independently 0, 1 or 2; and
  $M^+$ is a cation.

6. The method of claim 1, wherein the ionic liquid comprises 1-hexyl-3-methyl-imidazolium and the ion exchanger counterion is bisnonafluoro-1-butanesulfonimidate or bis((perfluorohexyl)sulfonyl)imide.

7. The method of claim 1, wherein the ion exchanger composition comprises a salt of the ion exchanger counterion selected from silver, lithium, sodium and potassium.

8. The method of claim 1, wherein the ion exchanger composition comprises a silver salt of the ion exchanger counterion and step (a) further comprises producing an insoluble silver salt.

9. The method according to claim 1, further comprising, prior to step (a), contacting the aqueous sample comprising the ionic liquid with a reverse phase substrate, thereby adsorbing proteins and/or lipids on the reverse phase substrate, if present in the aqueous sample.

10. The method according to claim 1, further comprising analyzing the aqueous eluate by mass spectrometry.

11. The method according to claim 1, further comprising:
  lysing cells of a biological sample; and
  contacting a biological sample with an amount of the ionic liquid sufficient to denature intracellular metabolic enzymes in the biological sample to produce the aqueous sample.

12. The method of claim 11, wherein the ionic liquid composition is an aqueous composition comprising 30% or more of the ionic liquid.

13. The method of claim 5, wherein the ionic liquid comprises 1-hexyl-3-methyl-imidazolium and the fluorinated ion exchanger counterion is bis((perfluorohexyl)sulfonyl)imide.

14. The method of claim 2, wherein the fluorous solvent is methoxyperfluorobutane.

15. The method of claim 9, further comprising eluting the proteins from the reverse phase substrate and analyzing the proteins by mass spectrometry.

* * * * *

UNITED STATES PATENT AND TRADEMARK OFFICE
CERTIFICATE OF CORRECTION

PATENT NO. : 9,958,363 B2
APPLICATION NO. : 14/724656
DATED : May 1, 2018
INVENTOR(S) : Brian Phillip Smart et al.

It is certified that error appears in the above-identified patent and that said Letters Patent is hereby corrected as shown below:

On the Title Page

On the page 2, In Column 2, under "Other Publications", Line 15, delete "Biphase" and insert -- Biphasic --, therefor.

In the Specification

In Column 2, Lines 8-9, delete "$Ag^+$-N(perfluorohexylsulfonyl)$_2$," and insert -- $Ag^+$N(perfluorohexylsulfonyl)$_2$; --, therefor.

Figure 7A:
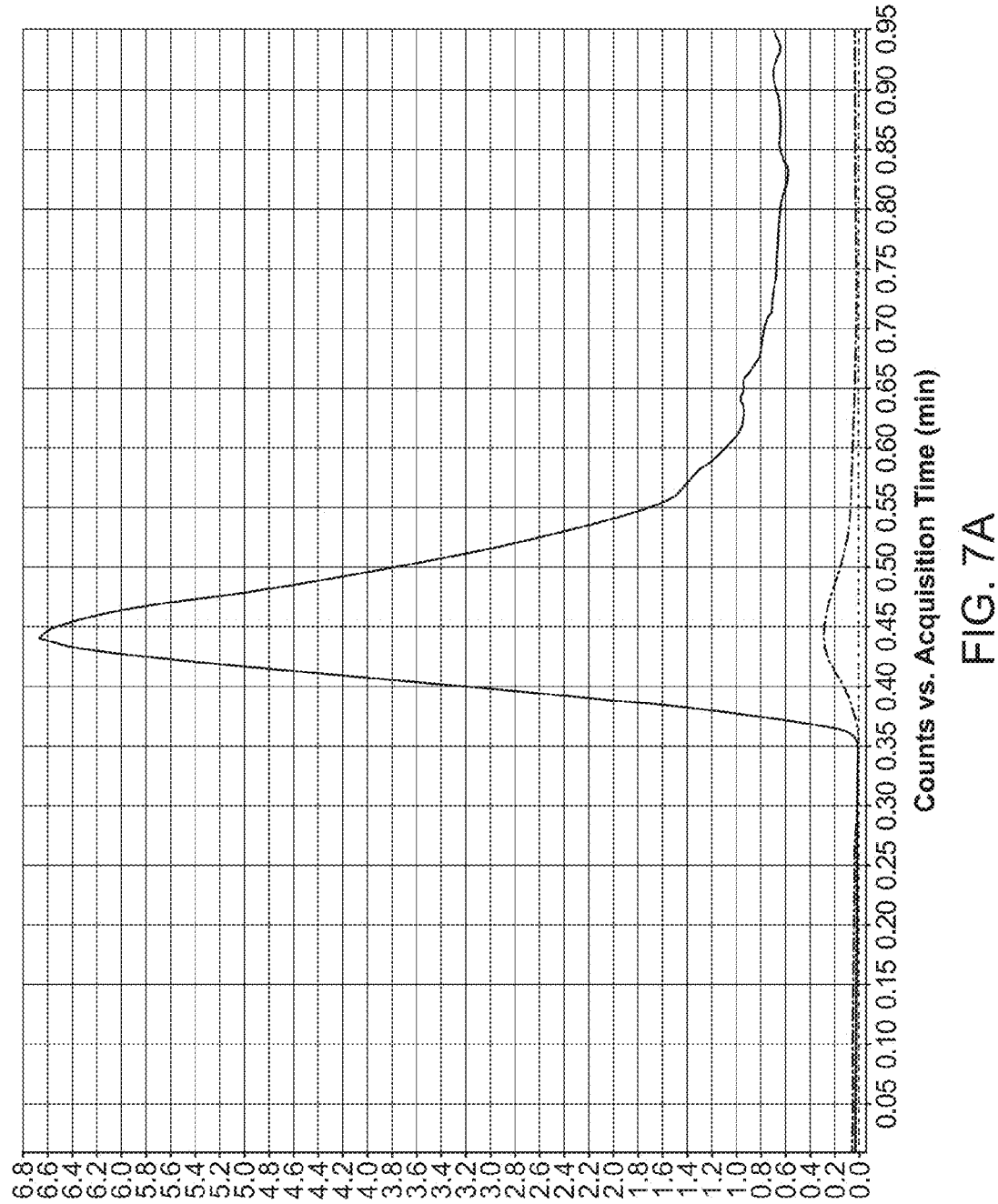
FIGS. 7A and 7b show extracted ion chromatograms (EIC) for HMIM after each extraction of the aqueous layer using fresh HFE-7100 (methoxyperfluorobutane) and bis((perfluorohexyl)sulfonyl)imide. (A) EIC for HMIM in a blank run (i), after the initial ion exchange reaction (ii), and two subsequent extractions (iii and iv). (B) The same EICs as in (A), with the initial ion exchange reaction EIC removed to demonstrate the levels go almost back to background.
Figure 7B:
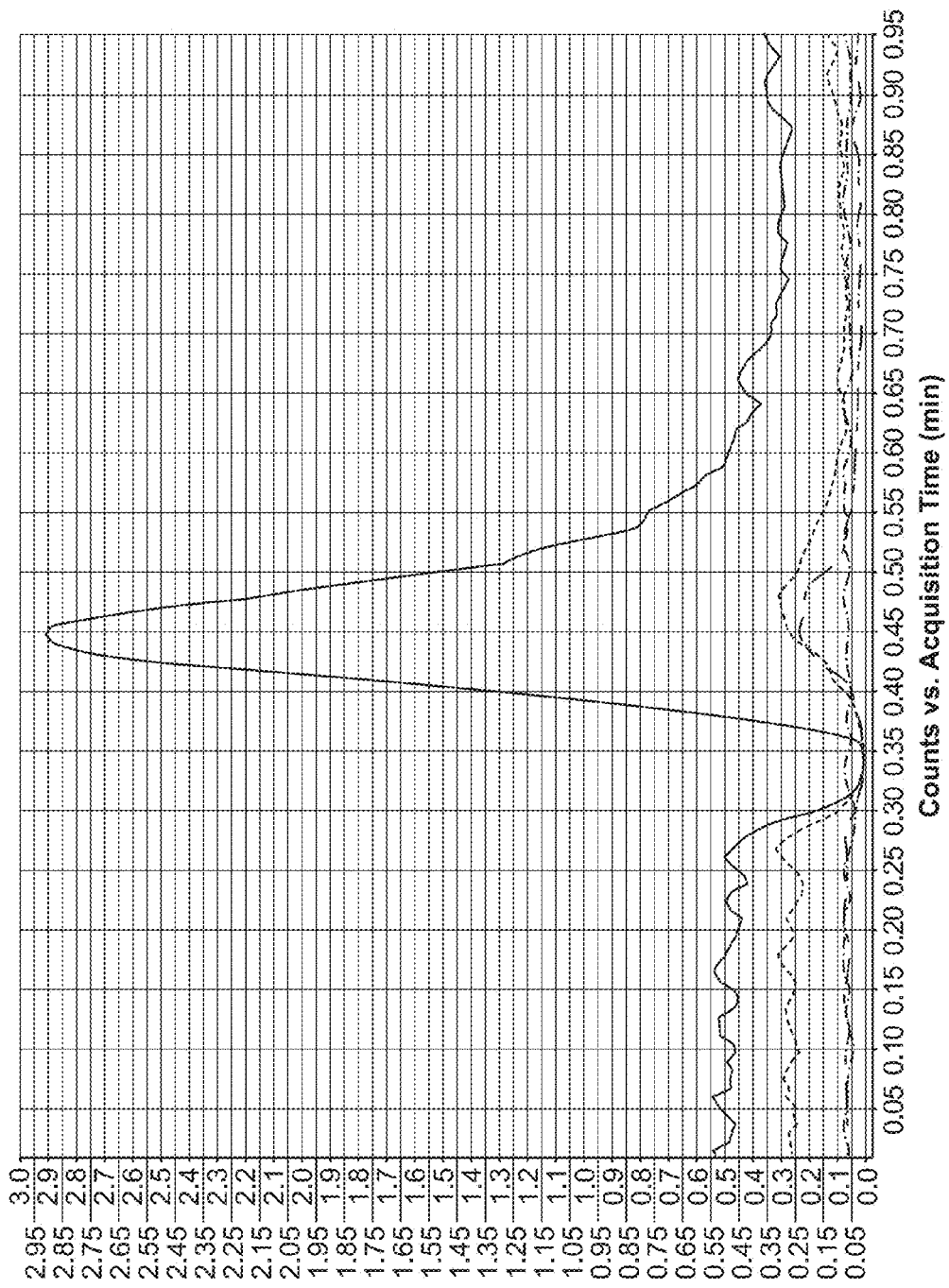
Figure 8A:
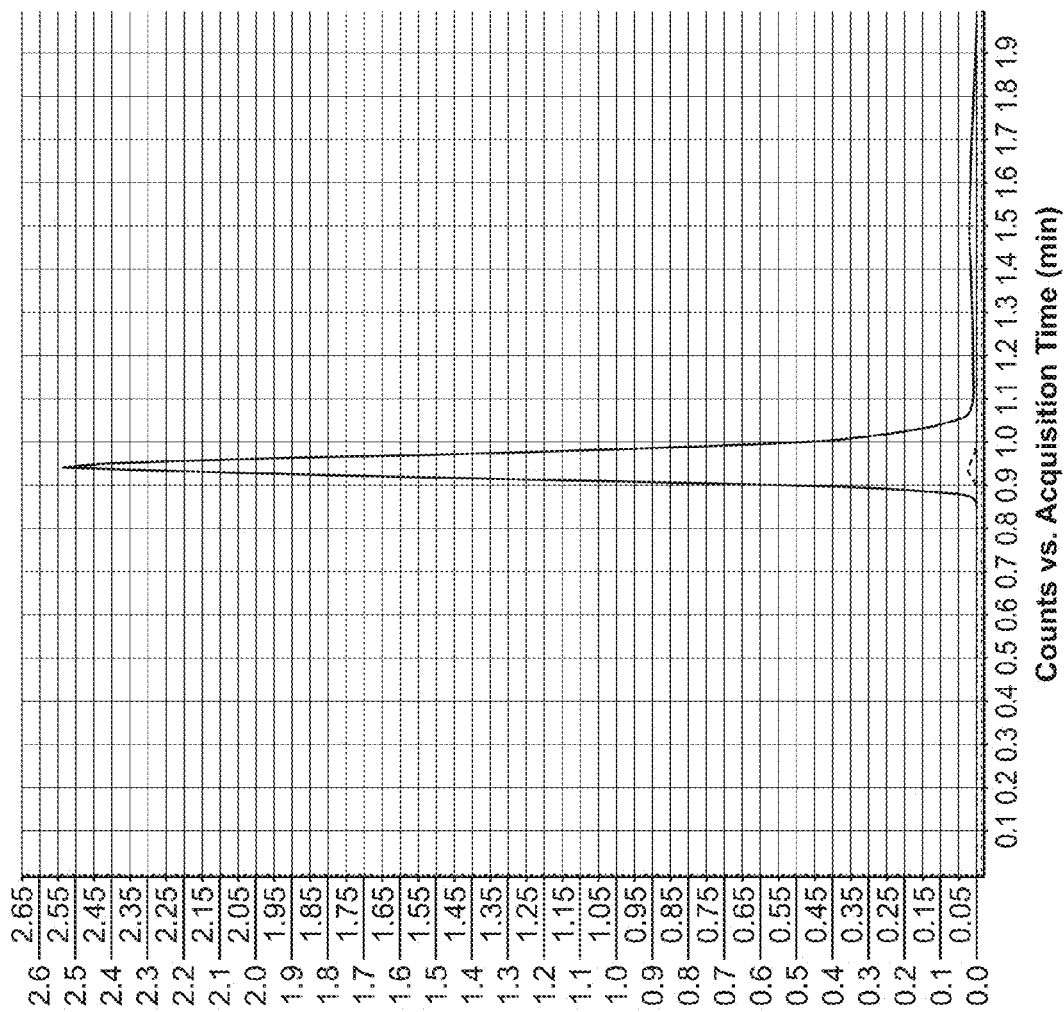
FIGS. 8A and 8B show EICs for bis((perfluorohexyl)sulfonyl)imide after each extraction of the aqueous layer using fresh HFE-7100 and bis((perfluorohexyl)sulfonyl)imide. (A) EICs for bis((perfluorohexyl)sulfonyl)imide in a blank run (i), after the initial ion exchange reaction (ii), and two subsequent extractions (iii and iv). (B) The same EICs as in (A), with the initial ion exchange reaction EIC removed to demonstrate the levels go almost back to background.
Figure 8B:
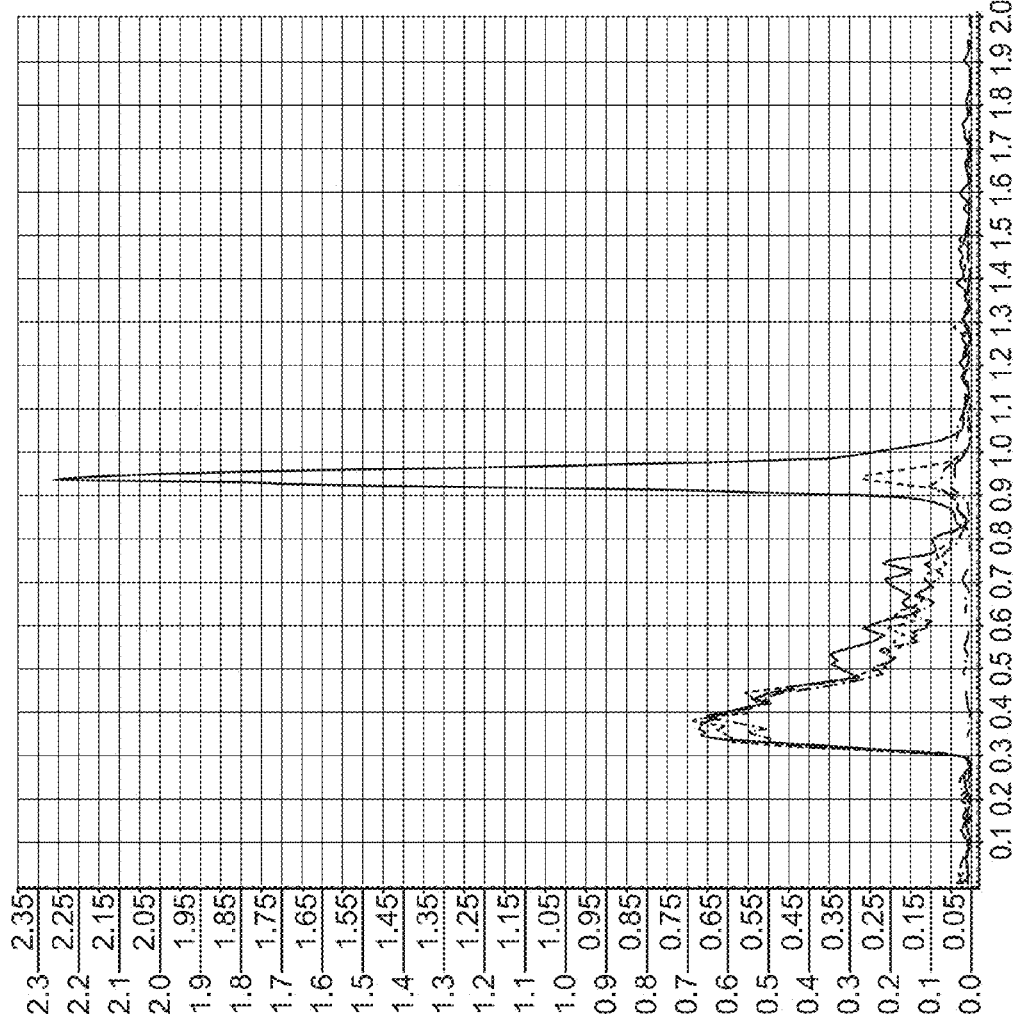

In Column 2, Line 28, delete "FIGS. 7 A and 7b" and insert -- FIGS. 7A and 7B --, therefor.

In Column 2, Line 49, delete "Exchager" and insert -- Exchanger --, therefor.

In Column 2, Line 60, delete "Nonelutropic" and insert -- Noneluotropic --, therefor.

In Column 3, Line 6, delete "Spin-" and insert -- Spin~ --, therefor.

In Column 5, Line 7, after "$^{11}C$," insert -- $^{13}C$, --.

In Column 7, Line 6, delete "-napthyl," and insert -- -naphthyl, --, therefor.

In Column 7, Line 7, delete "napthyl," and insert -- naphthyl, --, therefor.

In Column 7, Line 12, delete "phenylnapthyl," and insert -- phenylnaphthyl, --, therefor.

In Column 7, Line 53, delete "$R^{43}$," and insert -- $R^{43}$ --, therefor.

Signed and Sealed this
Second Day of October, 2018

Andrei Iancu
*Director of the United States Patent and Trademark Office*

CERTIFICATE OF CORRECTION (continued)
U.S. Pat. No. 9,958,363 B2

In Column 8, Line 19, delete "heterorylalkynyl" and insert -- heteroarylalkynyl --, therefor.

In Column 9, Lines 9-10, delete "—$NR^{62}C(O)NR^{60}R^{61}$," and insert -- —$NR^{62}C(O)NR^{60}R^{61}$, --, therefor.

In Column 9, Lines 27-28, delete "$P(O)(O^-)_2$," and insert -- —$P(O)(O^-)_2$, --, therefor.

In Column 9, Line 33, after "—$S(O)_2R^{60}$," insert -- —$P(O)(OR^{60})(O^-)$, --.

In Column 9, Line 37, after "—$S(O)_2R^{60}$," insert -- —$OP(O)(OR^{60})(OR^{61})$, --.

In Column 9, Line 37, delete "—C(O) $OR^{60}$," and insert -- —$C(O)OR^{60}$, --, therefor.

In Column 12, Lines 38-39, delete "fluororus" and insert -- fluorous --, therefor.

In Column 17, Line 52, delete "substitutents." and insert -- substituents. --, therefor.

In Column 20, Lines 35-37, delete " " and insert --  --, therefor.

In Column 23, Line 21, delete "a the" and insert -- a --, therefor.

In Column 24, Line 40, delete "acetylaldehyde," and insert -- acetaldehyde, --, therefor.

In Column 25, Line 62, delete "phophoglycerate" and insert -- phosphoglycerate --, therefor.

In Column 25, Line 67, delete "-bisphophate" and insert -- -bisphosphate --, therefor.

In Column 32, Line 9, delete "the a" and insert -- the --, therefor.

In Column 34, Line 19, delete "($^-$)$SO_2$" and insert -- ($^-$)-$SO_2$ --, therefor.

In Column 34, Line 20, delete "$Z^2$]. $M^+$" and insert -- $Z^2$].$M^+$ --, therefor.

In Column 35, Line 22, delete "($^-$)$SO_2$" and insert -- ($^-$)-$SO_2$ --, therefor.

In Column 41, Line 57, delete "($^-$)$SO_2$" and insert -- ($^-$)-$SO_2$ --, therefor.

In Column 43, Line 55, delete "metabololites" and insert -- metabolites --, therefor.

In Column 45, Line 37, after "components" insert -- . --.

In Column 45, Line 41, after "type" insert -- . --.

CERTIFICATE OF CORRECTION (continued)
U.S. Pat. No. 9,958,363 B2

In Column 46, Line 3, delete "elutropic" and insert -- eluotropic --, therefor.

In Column 46, Line 9, delete "Solublize" and insert -- Solubilize --, therefor.

In Column 47, Line 8, delete "elutropic" and insert -- eluotropic --, therefor.